(12) United States Patent
Madhuranthakam et al.

(10) Patent No.: US 11,896,815 B2
(45) Date of Patent: Feb. 13, 2024

(54) SYSTEMS, APPARATUSES AND METHODS FOR STABILIZING A USER'S BODY DURING DETECTED FALL EVENTS

(71) Applicant: Optum Technology, Inc., Eden Prairie, MN (US)

(72) Inventors: Aditya Madhuranthakam, Telangana (IN); Ninad D. Sathaye, Bangalore (IN); Gregory J. Boss, Saginaw, MI (US); Shyam Charan Mallena, Telangana (IN); V Kishore Ayyadevara, Telangana (IN); Sree Harsha Ankem, Telangana (IN)

(73) Assignee: Optum Technology, Inc., Eden Prairie, MN (US)

( * ) Notice: Subject to any disclaimer, the term of this patent is extended or adjusted under 35 U.S.C. 154(b) by 0 days.

(21) Appl. No.: 17/248,863

(22) Filed: Feb. 11, 2021

(65) Prior Publication Data

US 2022/0249837 A1    Aug. 11, 2022

Related U.S. Application Data

(63) Continuation of application No. 17/248,862, filed on Feb. 11, 2021.

(51) Int. Cl.
*A61N 1/36* (2006.01)
*A61B 5/00* (2006.01)
(Continued)

(52) U.S. Cl.
CPC .......... *A61N 1/0452* (2013.01); *A61B 5/4023* (2013.01); *A61N 1/0484* (2013.01);
(Continued)

(58) Field of Classification Search
CPC ...... A61N 1/0452; A61N 1/0484; A61N 1/08; A61N 1/321; A61N 1/36003;
(Continued)

(56) References Cited

U.S. PATENT DOCUMENTS

| 5,643,329 A | 7/1997 | Solomonow et al. |
|---|---|---|
| 10,052,062 B2 | 8/2018 | De Sapio et al. |

(Continued)

FOREIGN PATENT DOCUMENTS

CN    104825165 B    11/2017

OTHER PUBLICATIONS

"Position-Triggered Muscle Stimulator Prevents Falls For Wheelchair Users," Veterans Affairs, Louis Stokes Cleveland VA Medical Center, (5 pages), (Article, Online). [Retrieved from the Internet Apr. 6, 2021] <URL: https://techlinkcenter.org/technologies/position-triggered-muscle-stimulator-prevents-falls-for-wheelchair-users/757a747d-6b26-4a53-b0ce-83f3de8d22f3>.

(Continued)

*Primary Examiner* — Carl H Layno
*Assistant Examiner* — Jane C Kalinock
(74) *Attorney, Agent, or Firm* — Alston & Bird LLP

(57) ABSTRACT

Apparatuses, systems, and methods for more accurate remote monitoring of a user's body to stabilize the user during fall events and to thereby prevent the user from falling. In some embodiments, a wearable device comprising a power source, one or more sensors configured to monitor a user's COG (COG), at least one plurality of electrodes, a communications interface and a control device is provided. The wearable device is configured to apply electrical pulses according to defined electrical pulse stimulation protocols via the electrodes to target muscle groups of the user's body, causing those target muscle groups to contract and thereby stabilize the user's body during a fall event.

17 Claims, 10 Drawing Sheets

(51) Int. Cl.
*A61N 1/04* (2006.01)
*A61N 1/08* (2006.01)

(52) U.S. Cl.
CPC .......... *A61N 1/08* (2013.01); *A61N 1/36003* (2013.01); *A61N 1/36034* (2017.08)

(58) Field of Classification Search
CPC .......... A61N 1/36031; A61N 1/36034; A61B 5/1116; A61B 5/1117; A61B 5/112; A61B 5/1121; A61B 5/4023
USPC ................................................... 607/115, 48
See application file for complete search history.

(56) References Cited

U.S. PATENT DOCUMENTS

| | | | |
|---|---|---|---|
| 10,076,656 | B2 | 9/2018 | Dar et al. |
| 10,383,550 | B2 | 8/2019 | Hyde et al. |
| 2008/0147143 | A1 | 6/2008 | Popovic et al. |
| 2009/0216156 | A1 | 8/2009 | Lengsfeld et al. |
| 2013/0317400 | A1 | 11/2013 | Ferezy |
| 2017/0281054 | A1 | 10/2017 | Stever et al. |
| 2017/0303849 | A1 | 10/2017 | De Sapio et al. |
| 2018/0015284 | A1* | 1/2018 | Coleman ................ G16H 40/63 |
| 2018/0042654 | A1 | 2/2018 | Ingvarsson et al. |
| 2018/0071528 | A1 | 3/2018 | Fujiwara et al. |
| 2018/0132757 | A1* | 5/2018 | Kong ................... A61B 5/4836 |
| 2018/0140842 | A1* | 5/2018 | O Laighin ......... A61N 1/36003 |
| 2019/0099113 | A1 | 4/2019 | Röder et al. |
| 2019/0298998 | A1 | 10/2019 | Coleman et al. |
| 2020/0022832 | A1 | 1/2020 | Hyde et al. |
| 2020/0268287 | A1 | 8/2020 | Discenzo |
| 2022/0355107 | A1* | 11/2022 | Gozani ............. A61N 1/36021 |

OTHER PUBLICATIONS

Agarwal, Shubham et al. "Wearable Posture Corrector," Final Report For ECE 445, Senior Design, May 3, 2016, Project No. 39, (33 pages).

Armstrong, Kiley L. et al. "Automatic Application Of Neural Stimulation During Wheelchair Propulsion After SCI Enhances Recovery Of Upright Sitting From Destabilizing Events," Journal of NeuroEngineering and Rehabilitation, vol. 15, No. 1, Mar. 12, 2018, pp. 1-13. DOI: 10.1186/s12984-018-0362-2.

NonFinal Office Action for U.S. Appl. No. 17/248,862, dated Jan. 4, 2022, (19 pages), United States Patent and Trademark Office, USA.

Final Office Action for U.S. Appl. No. 17/248,862, dated Aug. 24, 2022, (19 pages), United States Patent and Trademark Office, US.

* cited by examiner

SYSTEMS, APPARATUSES AND METHODS FOR STABILIZING A USER'S BODY DURING DETECTED FALL EVENTS

CROSS-REFERENCE TO RELATED APPLICATIONS

This patent application is a continuation of U.S. patent application Ser. No. 17/248,862, filed Feb. 11, 2021, the contents of which are incorporated herein by reference in their entirety.

BACKGROUND

Various people, particularly elderly people, are prone to losing balance and falling, and these falls can periodically lead to serious and sometimes fatal injuries. Through applied effort, ingenuity, and innovation, various apparatuses, systems, and methods have been realized for decreasing a person's risk of falling when losing balance.

BRIEF SUMMARY

In general, embodiments of the present disclosure provide methods, apparatuses, systems, computing devices, computing entities, and/or the like for detecting and preventing falls in real-time.

In accordance with one aspect, a wearable device is provided. The wearable device is configured to: store, via a controller, a baseline center of gravity (COG) profile for a user, wherein the baseline COG profile defines a plurality of threshold COG offset values each corresponding to a body position and a body movement; generate COG data in real-time via one or more sensors of the wearable device; determine, via the controller, whether the COG data satisfies at least one threshold COG offset value of the plurality of threshold COG offset values; responsive to determining that the COG data satisfies at least one threshold COG offset value, identifying a first pulse stimulation protocol for a first plurality of electrodes of the wearable device and a second pulse stimulation protocol for a second plurality of electrodes of the wearable device, wherein (a) the first pulse stimulation protocol is defined based at least in part on the baseline COG profile and is configured to stimulate a first set of target muscles of the user's body, and (b) the second pulse stimulation protocol is defined based at least in part on the baseline COG profile and is configured to stimulate a second set of target muscles of the user's body; and responsive to identifying the first pulse stimulation protocol and the second pulse stimulation protocol, causing (a) the first plurality of electrodes to provide a first electrical pulse corresponding to the first pulse stimulation protocol, and (b) the second plurality of electrodes to provide a second electrical pulse corresponding to the second pulse stimulation protocol.

In accordance with another aspect, a method of stabilizing a user is provided. The method comprises: providing a wearable device around a waist of the user; storing, via a controller of the wearable device, a baseline center of gravity (COG) profile for a user, wherein the baseline COG profile defines a plurality of threshold COG offset values each corresponding to a body position and a body movement; generating COG data in real-time via one or more sensors of the wearable device; determining, via the controller, whether the COG data satisfies at least one threshold COG offset value of the plurality of threshold COG offset values; responsive to determining that the COG data satisfies at least one threshold COG offset value, identifying a first pulse stimulation protocol for a first plurality of electrodes of the wearable device and a second pulse stimulation protocol for a second plurality of electrodes of the wearable device, wherein (a) the first pulse stimulation protocol is defined based at least in part on the baseline COG profile and is configured to stimulate a first set of target muscles of the user's body, and (b) the second pulse stimulation protocol is defined based at least in part on the baseline COG profile and is configured to stimulate a second set of target muscles of the user's body; and responsive to identifying the first pulse stimulation protocol and the second pulse stimulation protocol, causing (a) the first plurality of electrodes to provide a first electrical pulse corresponding to the first pulse stimulation protocol, and (b) the second plurality of electrodes to provide a second electrical pulse corresponding to the second pulse stimulation protocol.

In accordance with yet another aspect, a computer program product is provided. The computer program product comprises a non-transitory computer readable medium having computer program instructions stored therein, the computer program instructions when executed by a processor, cause the processor to: store a baseline center of gravity (COG) profile for a user, wherein the baseline COG profile defines a plurality of threshold COG offset values each corresponding to a body position and a body movement; store COG data generated in real-time via one or more sensors of a wearable device; determine whether the COG data satisfies at least one threshold COG offset value of the plurality of threshold COG offset values; responsive to determining that the COG data satisfies at least one threshold COG offset value, identify a first pulse stimulation protocol for a first plurality of electrodes of the wearable device and a second pulse stimulation protocol for a second plurality of electrodes of the wearable device, wherein (a) the first pulse stimulation protocol is defined based at least in part on the baseline COG profile and is configured to stimulate a first set of target muscles of the user's body, and (b) the second pulse stimulation protocol is defined based at least in part on the baseline COG profile and is configured to stimulate a second set of target muscles of the user's body; and responsive to identifying the first pulse stimulation protocol and the second pulse stimulation protocol, cause (a) the first plurality of electrodes to provide a first electrical pulse corresponding to the first pulse stimulation protocol, and (b) the second plurality of electrodes to provide a second electrical pulse corresponding to the second pulse stimulation protocol.

In accordance with yet another aspect, a wearable device is provided. The wearable device comprises: a webbing extending between a first end and a second end, wherein the first end and the second end comprise fastening components that interact to enable connection between the first end and the second end to secure the webbing around a user's waist such that the webbing defines an interior surface to be placed against a user's body and an opposite exterior surface when the first end is connected with the second end; a controller secured to the webbing; one or more sensors in electronic communication with the controller, wherein the one or more sensors are secured to the webbing and configured to generate center of gravity (COG) data indicative of the user's balance; a first plurality of electrodes secured on the interior surface of the webbing, wherein the first plurality of electrodes are in electronic communication with the controller and the first plurality of electrodes are configured to apply an electrical pulse stimulation protocol configured to stimulate a first target muscle group of a user upon receipt of signals from the controller; and a second plurality of electrodes secured on the interior surface of the webbing, wherein the second plurality of electrodes are in electronic communication with the controller and the second plurality of electrodes are configured to apply an electrical pulse stimulation protocol configured to stimulate a second target muscle group of the user upon receipt of signals from the controller.

In accordance with yet another aspect, a method of stabilizing a user's body is provided. The method comprises providing a wearable device around a waist of the user, the wearable device comprising: a webbing extending between a first end and a second end, wherein the first end and the second end comprise fastening components that interact to enable connection between the first end and the second end to secure the webbing around a user's waist such that the webbing defines an interior surface to be placed against a user's body and an opposite exterior surface when the first end is connected with the second end; a controller secured to the webbing; one or more sensors in electronic communication with the controller, wherein the one or more sensors are secured to the webbing and configured to generate center of gravity (COG) data indicative of the user's balance; a first plurality of electrodes secured on the interior surface of the webbing, wherein the first plurality of electrodes are in electronic communication with the controller and the first plurality of electrodes are configured to apply an electrical pulse stimulation protocol configured to stimulate a first target muscle group of the user upon receipt of signals from the controller; and a second plurality of electrodes secured on the interior surface of the webbing, wherein the second plurality of electrodes are in electronic communication with the controller and the second plurality of electrodes are configured to apply an electrical pulse stimulation protocol configured to stimulate a second target muscle group of the user upon receipt of signals from the controller; monitoring COG data generated by the one or more sensors via the controller; determining, via the controller, whether the COG data satisfies at least one threshold COG offset value of a plurality of COG offset values; responsive to determining that the COG data satisfies at least one threshold COG offset value, identifying a first pulse stimulation protocol for a first plurality of electrodes of the wearable device and a second pulse stimulation protocol for a second plurality of electrodes of the wearable device, wherein (a) the first pulse stimulation protocol is defined within a baseline COG profile and is configured to stimulate a first set of target muscles of the user's body, and (b) the second pulse stimulation protocol is defined within the baseline COG profile and is configured to stimulate a second set of target muscles of the user's body; and responsive to identifying the first pulse stimulation protocol and the second pulse stimulation protocol, causing (a) the first plurality of electrodes to provide a first electrical pulse corresponding to the first pulse stimulation protocol, and (b) the second plurality of electrodes to provide a second electrical pulse corresponding to the second pulse stimulation protocol.

BRIEF DESCRIPTION OF THE DRAWINGS

Figure 1:
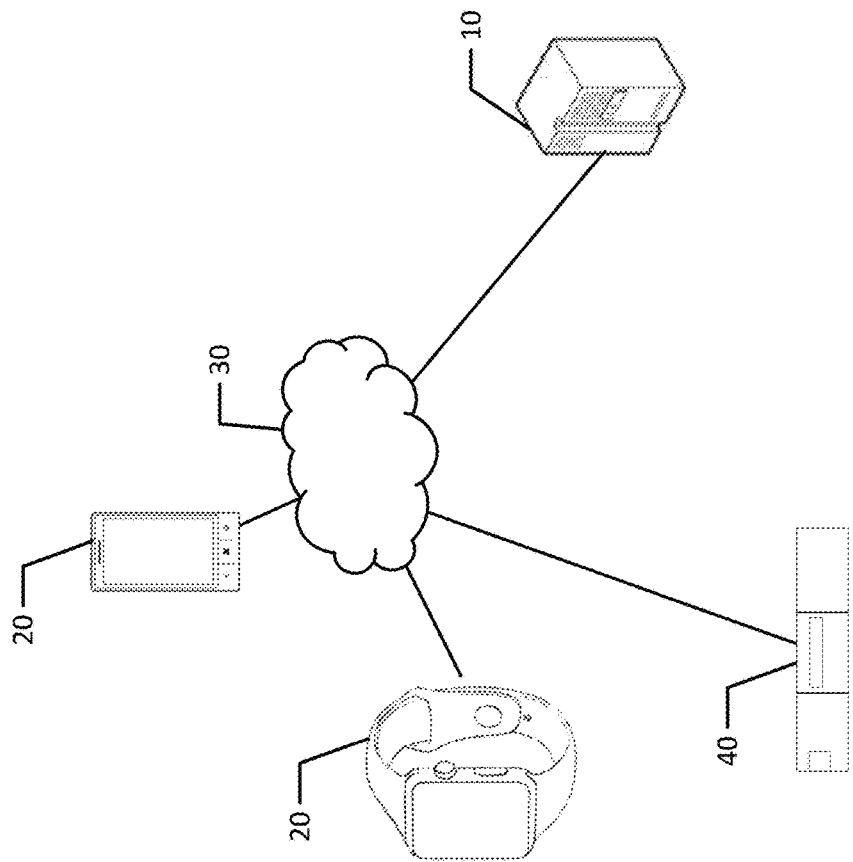
Figure 2:
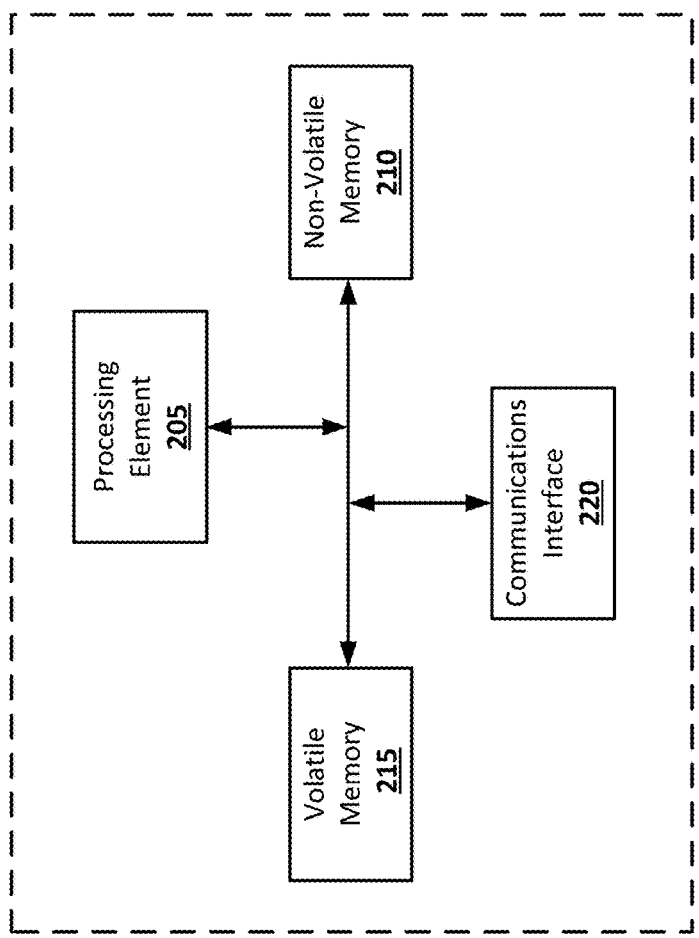
Figure 3:
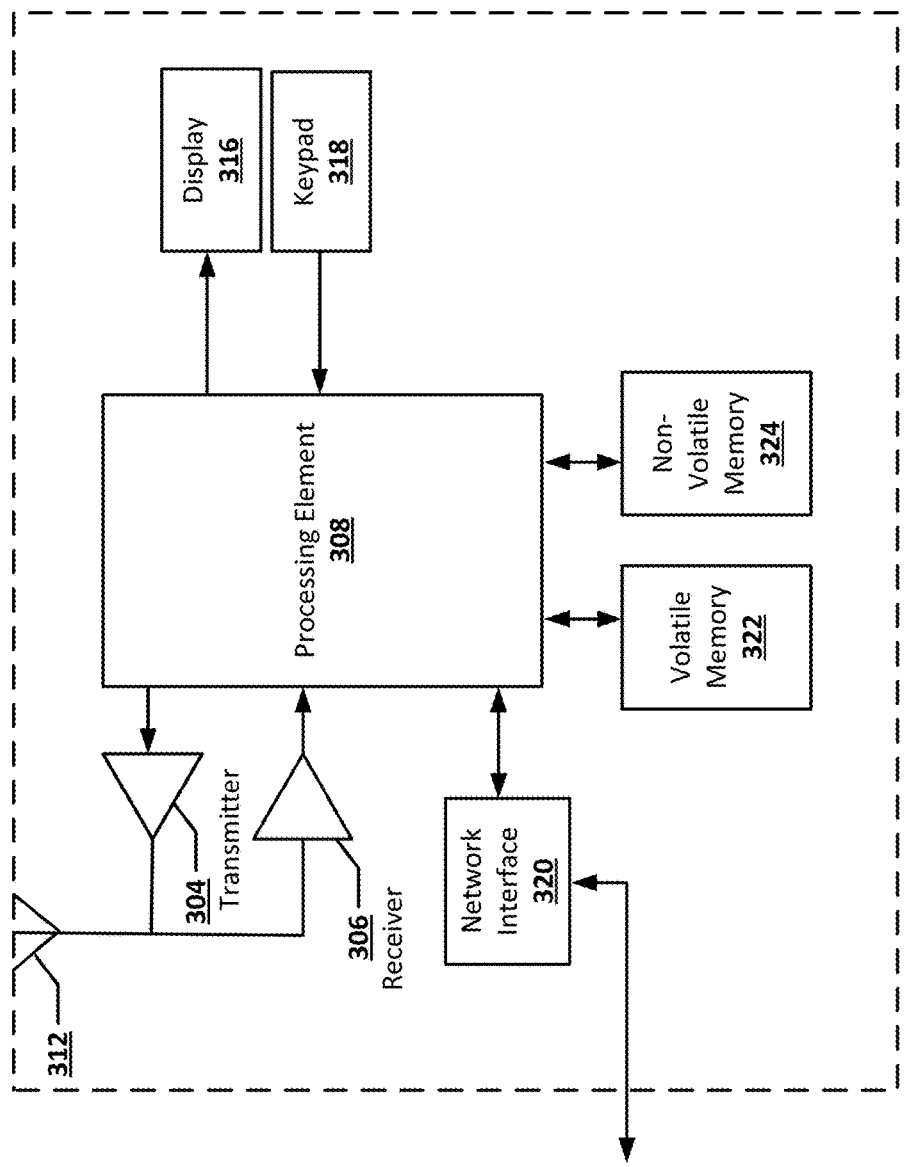
Figure 4A:
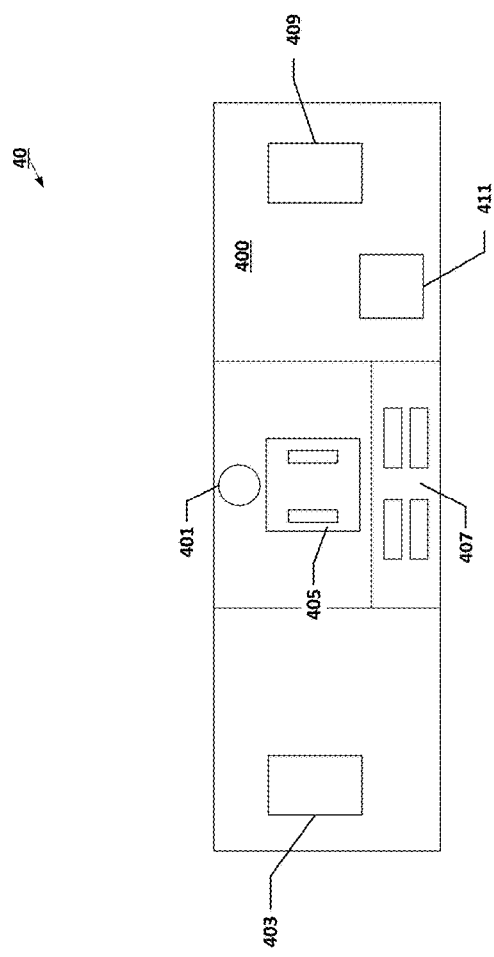
Figure 4B:
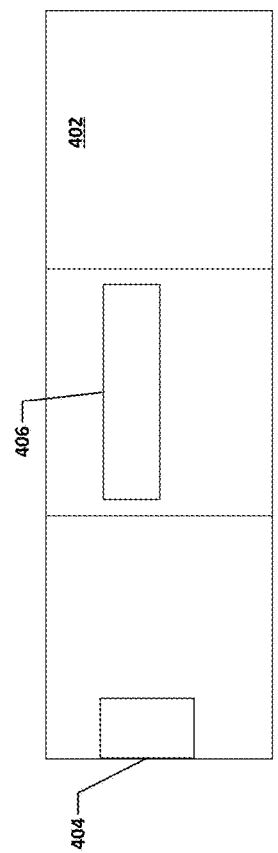
Figure 5:
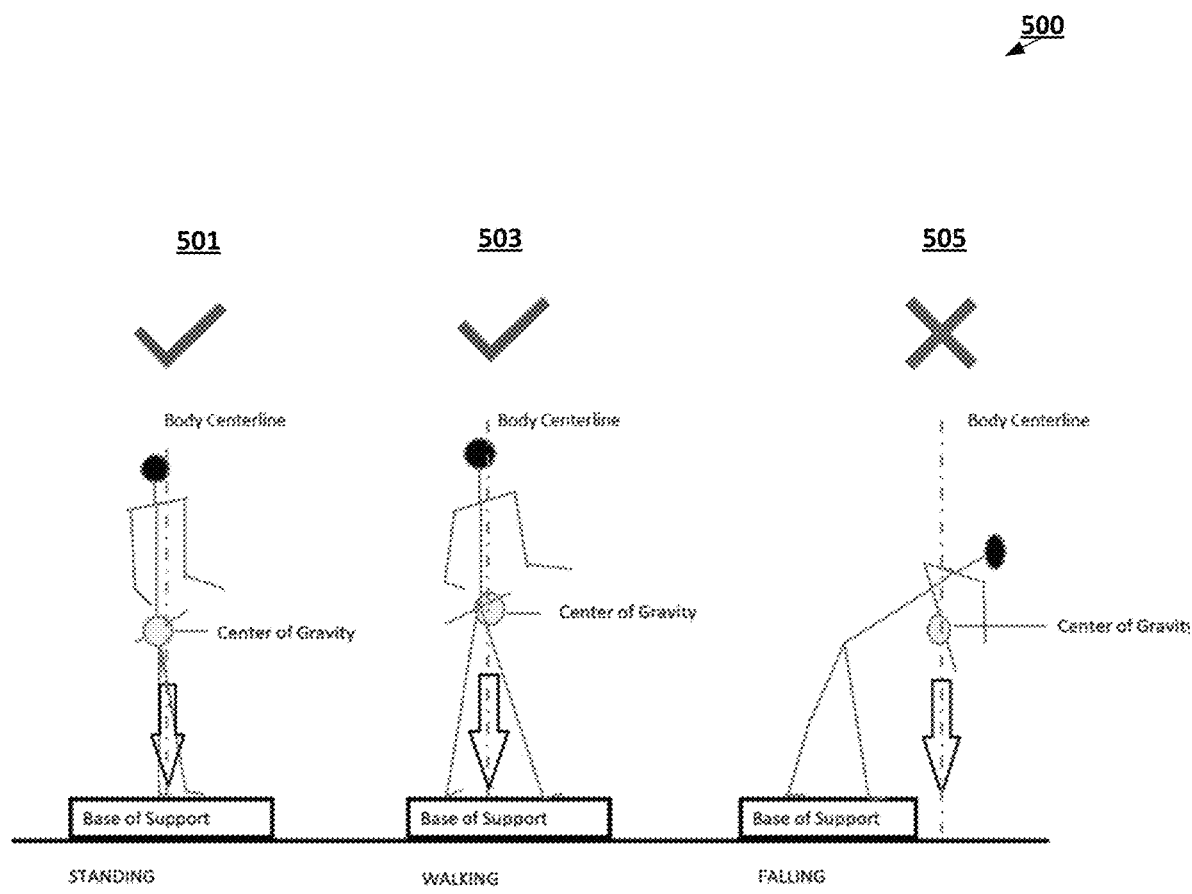
Figure 6:
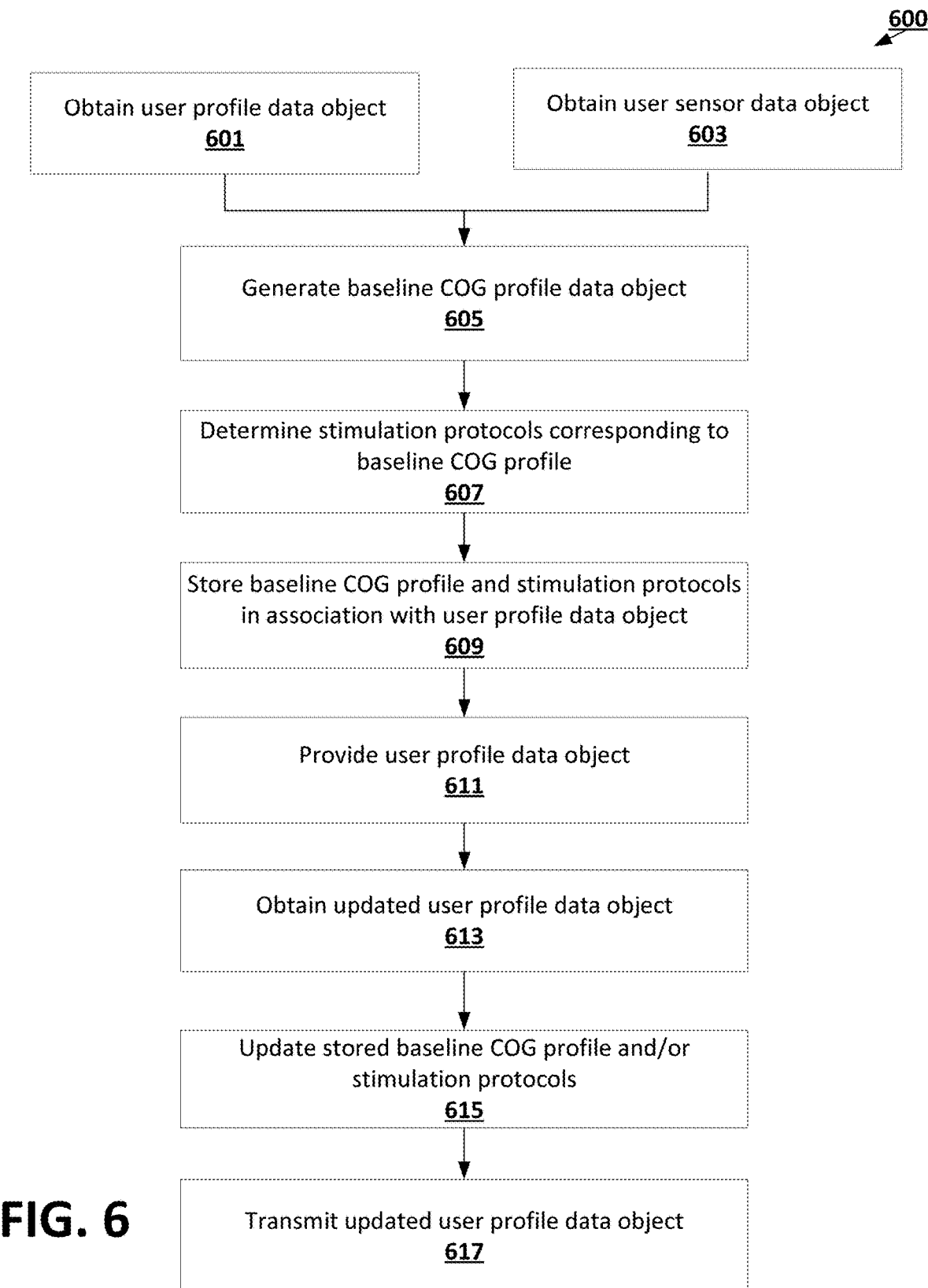
Figure 7:
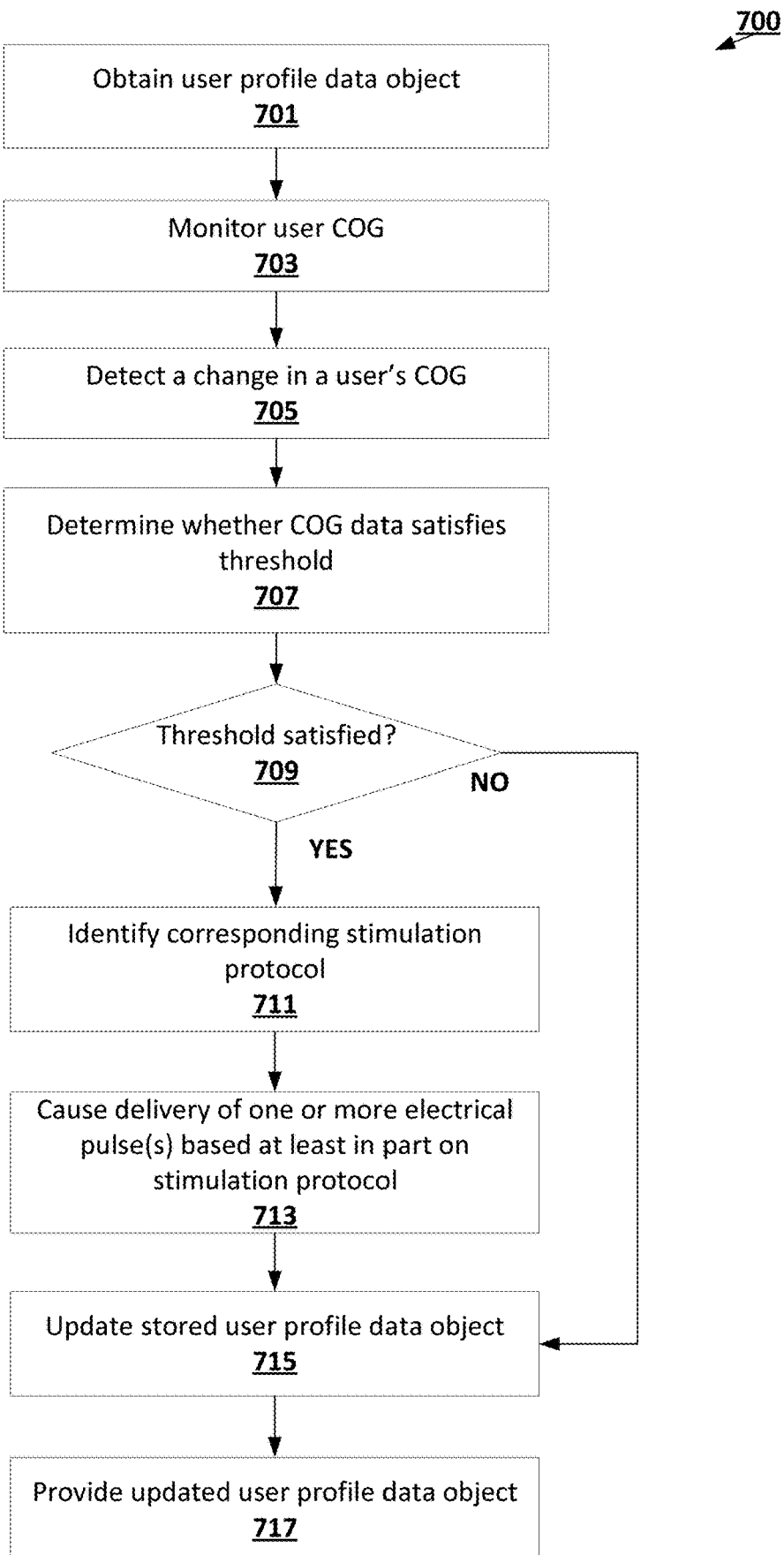
Figures 8A, 8B:
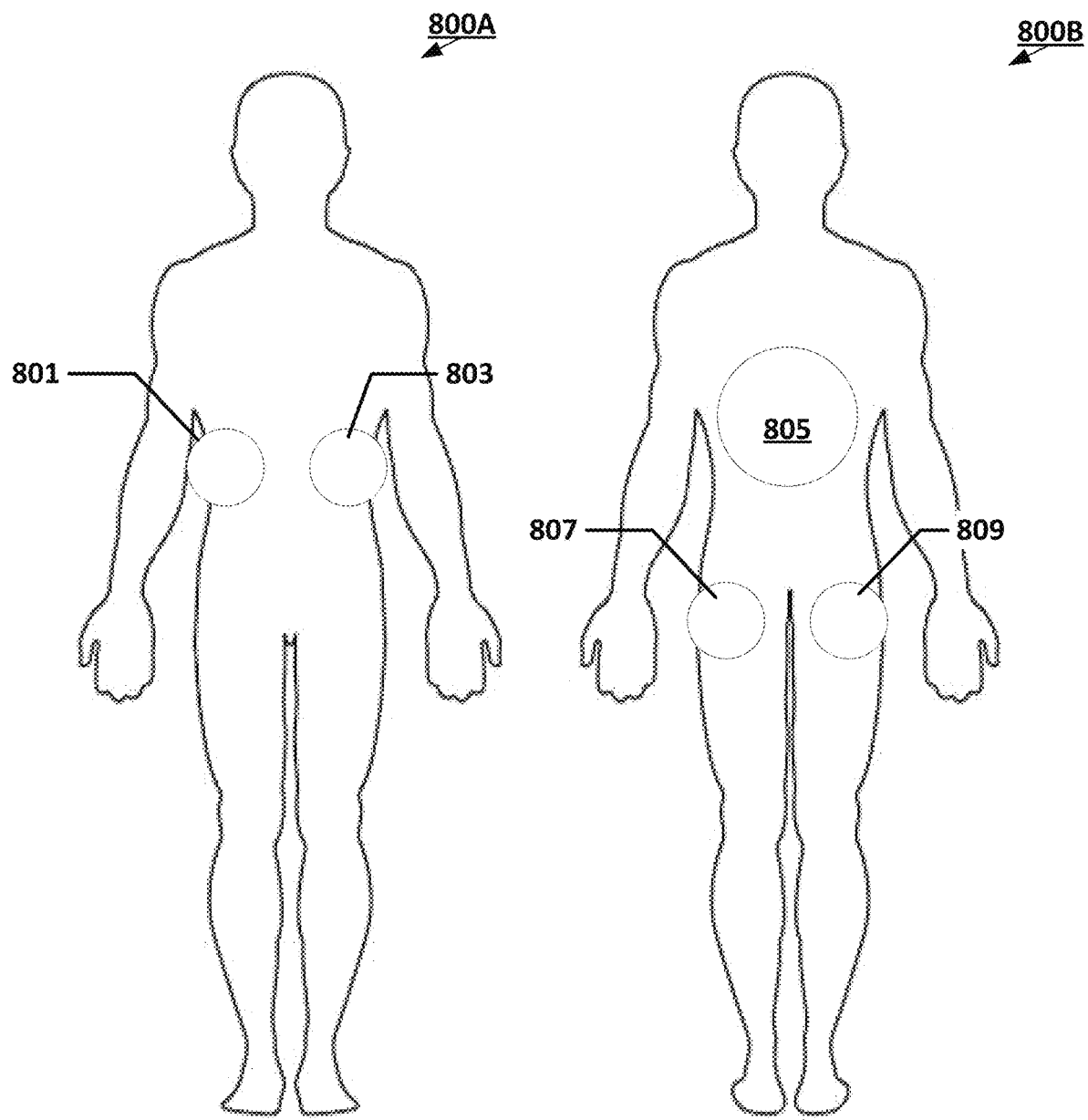
Figure 9:
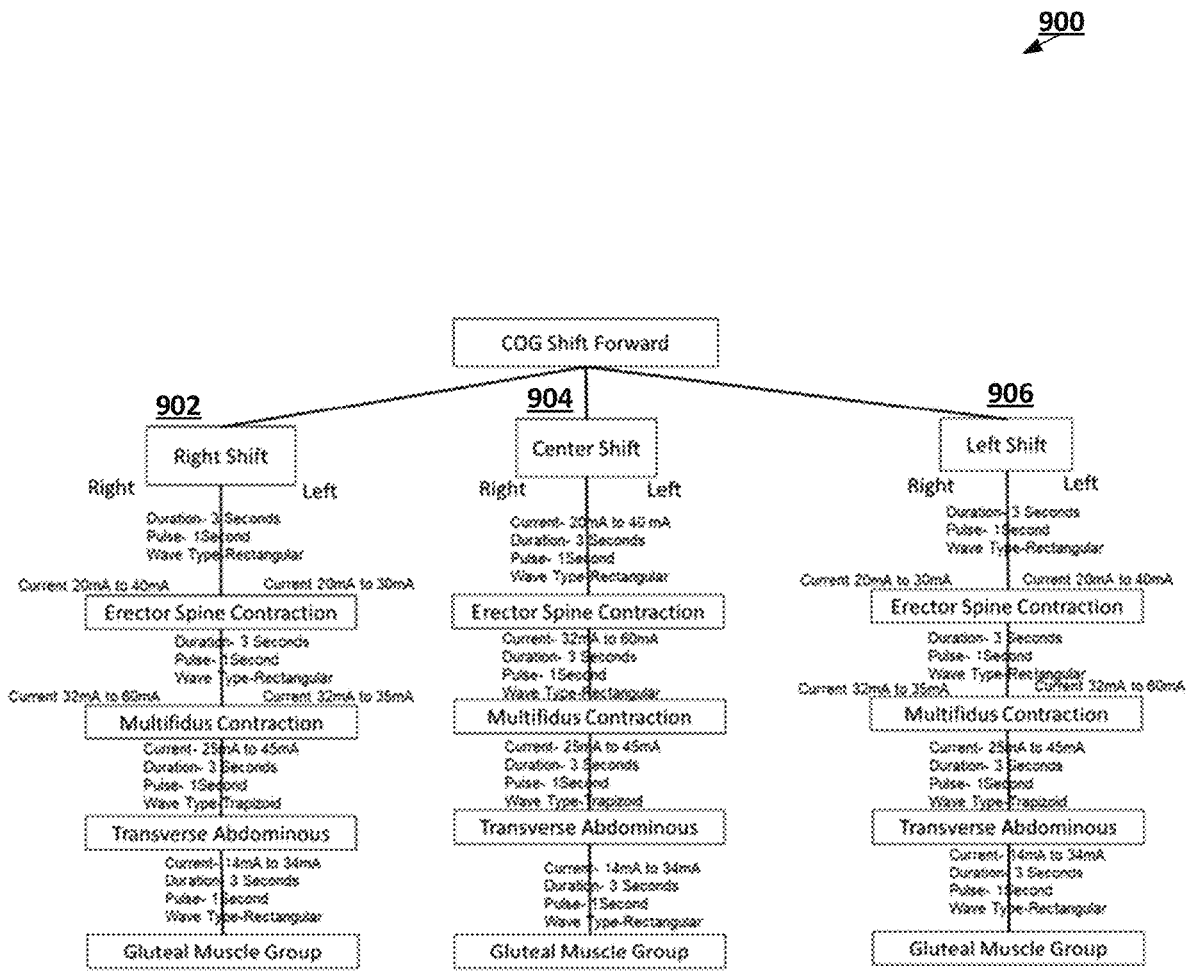
Figure 10:
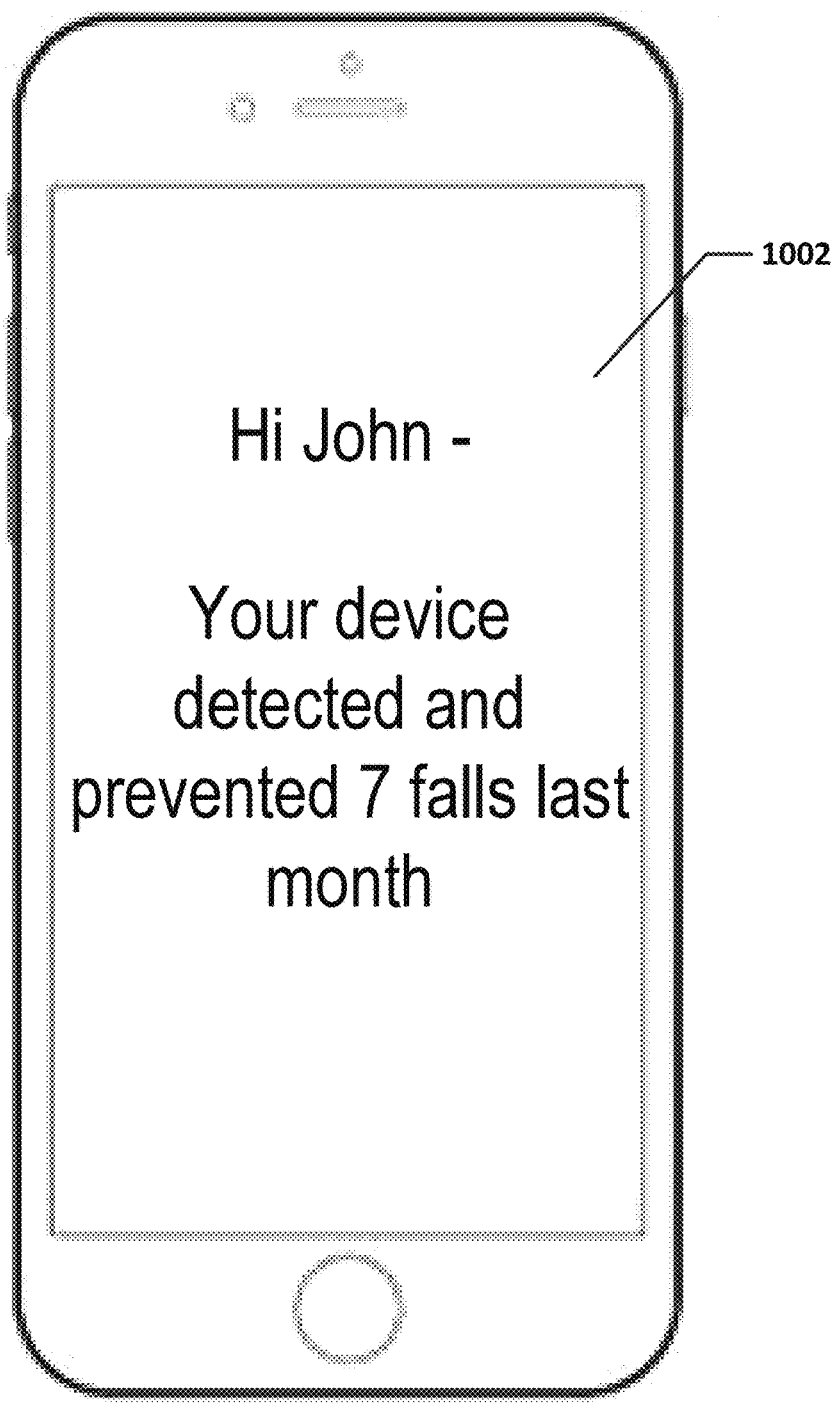

Having thus described the invention in general terms, reference will now be made to the accompanying drawings, which are not necessarily drawn to scale, and wherein:

FIG. 1 is an exemplary overview of a system architecture that can be used to practice various embodiments of the present disclosure;

FIG. 2 is an example schematic of a management computing entity in accordance with certain embodiments of the present disclosure;

FIG. 3 is an example schematic of a user computing entity in accordance with certain embodiments of the present disclosure;

FIGS. 4A and 4B are exemplary schematic illustrations of a wearable device, in accordance with certain embodiments of the present disclosure;

FIG. 5 is an example schematic illustration showing a person's center of gravity in various body positions, in accordance with certain embodiments of the present disclosure;

FIG. 6 is a flowchart diagram illustrating an example process for obtaining a user profile data object to a wearable device, in accordance with certain embodiments of the present disclosure;

FIG. 7 is a flowchart diagram illustrating an example process for stabilizing a user's body, in accordance with certain embodiments of the present disclosure;

FIGS. 8A and 8B are example schematics of a human body illustrating points of stimulation provided by a wearable device, in accordance with certain embodiments of the present disclosure;

FIG. 9 is an example hierarchy illustrating application of stimulation pulses, in accordance with certain embodiments of the present disclosure; and FIG. 10 is an example view of a user interface, in accordance with certain embodiments of the present disclosure.

DETAILED DESCRIPTION

Various embodiments of the present disclosure now will be described more fully hereinafter with reference to the accompanying drawings, in which some, but not all embodiments are shown. Indeed, various configurations as discussed herein may be embodied in many different forms and should not be construed as limited to the embodiments set forth herein; rather, these embodiments are provided so that this disclosure will satisfy applicable legal requirements. The term "or" (also designated as "I") is used herein in both the alternative and conjunctive sense, unless otherwise indicated. The terms "illustrative" and "exemplary" are used to be examples with no indication of quality level. Like numbers refer to like elements throughout.

I. OVERVIEW

Various embodiments are directed to systems, apparatuses, and/or methods for detecting a user's fall event and stabilizing the user's body to prevent the user from falling. There is a need for systems and techniques for stabilizing a user's body to prevent the user from falling in real-time, in particular for elderly and vulnerable persons. Existing devices are inadequate for preventing falls. For example, existing systems and techniques are unable to monitor a user's body positioning, movement, and center-of-gravity (COG) in real-time in order to detect an imminent fall such that the device can intervene to prevent the user from falling (e.g., by identifying target muscles corresponding with the type of fall and delivering electrical pulses to the target muscles to activate those muscles to stabilize the user's body and to counteract movement of the user's center of gravity in a way that prevents the user from falling).

There is also need for systems and techniques for monitoring a user's body in order to detect when a user's body should be stabilized to prevent falls that account for individual user characteristics and requirements including user response to interventions (e.g., stimulation) over time.

Various embodiments of the present disclosure are directed to a wearable device (e.g., a wearable belt) having an integrated controller and electrodes that are collectively configured to detect potential fall events and to stabilize the user's body to prevent falls in real-time based at least in part on identifying a change in a user's COG. In some embodiments, in response to detection of a user COG change or shift, the controller, together with the electrodes, delivers electrical pulses to the user's body (e.g., specifically to identified target muscles within the user's body) to induce contractions in target muscles of the body in order to stabilize the user's body to prevent a fall. In some embodiments, a baseline COG profile of a user and pulse stimulation protocols corresponding with various user body positions and/or body movements may be determined. In some embodiments, based at least in part on characteristics of a detected COG change or shift, a corresponding pulse stimulation protocol and one or more target muscles or target muscle groups may be identified. At least one plurality of electrodes within a wearable device may be caused to deliver one or more electrical pulses based at least in part on the identified pulse stimulation protocol. A pulse stimulation protocol may be dynamically adjusted (e.g., in real-time) based at least in part on user input and/or by monitoring user response. Additionally, the baseline COG profile of a user may be refined over time to identify optimal parameters for pulse stimulation protocols. To further enhance system performance, the wearable device may be calibrated based at least in part on user characteristics (e.g., age, gender, muscle condition and/or the like) and any changes thereto.

The apparatuses, systems, and methods described herein provide a robust fall detection and fall prevention system. Accordingly, various embodiments of the present disclosure make substantial technical contributions to the field of monitoring devices and substantially improve state-of-the-art systems.

II. DEFINITIONS OF CERTAIN TERMS

The term "wearable device" may refer to an article or garment configured to fit closely to a wearer's body proximate or adjacent to particular muscles to be activated through electrical pulses as discussed herein. In the configurations discussed in detail herein, a wearable device is be embodied as a belt configured to fit around a user's waist such that electrodes within the belt are proximate muscles within the user's back (e.g., erector spine, multifidus), the user's abdominals (e.g., internal obliques, external obliques, transverse abdominis, rectus abdominis), and/or the user's hips (e.g., gluteus maximus, gluteus medius, gluteus minimus), thereby enabling the electrodes within the wearable device to provide electrical pulses to those muscles. In other example embodiments, a wearable device may be embodied as a jacket, vest, shirt, pants, shorts, underwear, body wrap, and/or the like. Such alternative example wearable devices may additionally position electrodes proximate the musculature discussed above when worn by a user. An example wearable device may comprise at least a power source, a controller or processor, a wireless communication transceiver, an electrical pulse generator, one or more sensors (e.g., accelerometers, pressure sensors and/or the like) and at least one plurality of electrodes.

The term "center of gravity" or COG may refer to a reference location (e.g., point, center line and/or the like) at which the entire weight of an object can be balanced and/or about which the weight of the object may be considered to be concentrated with respect to a base of support. Accordingly, an object that is adequately supported with its COG aligned with at least a portion of its base of support will remain in a stable balance in a given position. With reference to a human body (e.g., person, individual, patient, user, body and/or the like used interchangeably herein) the COG may be a reference location (e.g., point, center line and/or the like) at which the weight of the body (e.g., torso) can be considered to be concentrated with respect to a base of support (e.g., the feet). For example, in order to remain upright while in a standing position, a balance between gravity pulling the body (e.g., torso) downward and the reaction force from the floor upward through the base of support (e.g., feet) which counteracts gravity is required. The muscles of the body also act to maintain a steady COG with respect to the body's base of support. For example, muscles may contract in response to forces acting a person's body and/or a shift in the body's COG in order to adjust (e.g., shift, restore or the like) the COG and remain in balance.

A body's COG is not fixed and varies in accordance with the body's movements and body position. For example, a person's COG will differ when the person is in a standing position as opposed to when the person is squatting. In another example, when a person is walking, the COG changes based at least in part on the person's changing gait and/or stride. Other parameters may affect a person's ability to maintain a stable COG (i.e., maintain balance in different body positions and/or while in motion) such as, without limitation, age, gender, clinical condition(s), body weight and weight distribution, height, body mass index, body fat composition, muscle condition, gait pattern and/or the like. For example, a tall person in a standing position may have a COG that is located higher (i.e., a greater distance from the ground) relative to the COG of a short person in a standing position. Accordingly, maintaining a steady COG (i.e., balance) while in a standing position may be more difficult for a tall person than it is for a short person. When a person's COG shifts in an anterior, posterior or lateral direction away from the person's base of support, the muscles of the body may react (e.g., contract) in order to maintain balance and avoid a resultant fall. The COG (e.g., center line) for forward movement (anterior flexion) of the trunk is approximately a line passing through the arthrodial joints of the foot. By way of example, if a person's torso flexes forward so that the COG of the trunk is located outside of the perimeter of the base, the person is likely to fall.

The term "base of support" may refer to an area of contact beneath an object or human body that includes every point of contact that the object or person makes with a supporting surface. These points of contact may be body parts (e.g., feet or hands) or may include objects such as crutches, a chair that the body is sitting in and the like. By way of example, a person in a standing position with his or her feet close together has a smaller base of support than the same person in a standing position with his or her feet wide apart. A person with a smaller base of support is more likely to lose his or her balance in response to a force acting on the body than a person with a larger base of support. Said differently, for any given body, maintaining a steady COG in a standing position (i.e., balance) is more difficult when the feet are together that when the feet are further apart from one another.

The term "fall" or "fall event" may refer to a biomechanical event with respect to a body during which the body's COG is misaligned with respect to the body's base of support. For example, an external force (e.g., gravity) may destabilize the body's COG resulting in misalignment of the weight of the body (e.g., torso) over the base of support (e.g., legs, feet). A fall may occur when a body's COG moves sufficiently far away (e.g., in an anterior, posterior or lateral direction) from the base of support provided by the feet against the floor.

The term "baseline COG profile" may refer to a plurality of configurable threshold COG offset values (e.g., automatically configurable or manually configurable threshold COG offset values) associated with a particular user in which each COG offset value is associated with a particular body movement and/or body position. A person's COG may vary depending on their current body position. For example, a person's COG while standing upright may be different from the person's COG while walking such that the reference location (e.g., point, center line and/or the like) defining the COG is different for each respective body position and/or body movement.

The term "COG offset value" may refer to an established (e.g., allowed, permissible or the like) displacement value/amount (e.g., tilt, angle, distance and/or the like) from a baseline or threshold COG value corresponding with a respective body position and/or body movement. In some embodiments, the COG offset value may be determined based at least in part on additional parameters associated with the user, including, without limitation, age, gender, body weight, height, muscle condition and/or the like. When a person's COG corresponding with a particular body position and/or body movement exceeds or is close to (e.g., within a predetermined range of) the COG offset value, it is likely that the person will lose his or her balance which may result in a fall.

The term "target muscle group" may refer to a one or more muscles associated with an area of the body that act to stabilize the person's body and/or otherwise maintain a steady COG with respect to a person's base of support. In response to forces acting on a person's body and/or a shift in the body's COG, one or more muscles within a particular target muscle group may contract in order to maintain a steady COG and restore balance (i.e., prevent the person from falling). For example, a back body area may be associated with a target muscle group including one or more back muscles (e.g., erector spine (e.g., spinalis, longissimus and/or iliocostalis muscles). In another example, an abdominal body area may be associated with a target muscle group including one or more abdominal muscles (e.g., internal oblique, external oblique, transverse abdominis and/or rectus abdominis muscles). In yet another example, a back body area may be associated with a target muscle group including one or more back or hip muscles (e.g., gluteus maximus, gluteus medius and/or gluteus minimus muscles). Target muscle groups and characteristics of the muscle contractions may vary in response to the incident COG shift. For example, in response to forward movement (anterior flexion) occurring on a left side of a body, a corresponding left portion of the longissimus muscle may contract. In response to forward movement (anterior flexion) occurring on a right side of the body, a corresponding right portion of the longissimus muscle may contract. In response to centered forward movement (anterior flexion), the entirety of the longissimus muscle may contract. Additionally, a muscle may contract more intensely if a rate of acceleration associated with a fall is greater.

The term "electrical pulses" may refer to electrical stimulation such as neuromuscular electrical stimulation (MMES) provided (e.g., delivered, applied or the like) to motor nerves in order to excite muscular tissue and induce muscle contractions. In some embodiments, electrical pulses may be provided in order to condition (e.g., strengthen, train) muscles. Muscular weakness and fatigue can impede a person's capacity for movement leading to reduced mobility and a propensity for loss of balance and stability. An electrical pulse may be defined by one or more characteristics (i.e., electrical pulse characteristics) including, without limitation, intensity (e.g., defined by amplitude, voltage and/or current characteristics), duration (e.g., pulse duration), wave type and/or wave form (e.g., rectangular, triangular, square, sawtooth and the like). Electrical pulses may be delivered to at least one muscle or target muscle group via electrode(s) positioned adjacent the respective muscle or target muscle group. In certain embodiments, electrical pulses may be provided at a voltage between 30-80V, a current between 10 mA-60 mA, a duration between 0.1 ms to 3 seconds. Electrical pulses may be provided in a variety of wave form shapes to provide adequate contraction to the target muscles to assist the user in regaining his/her balance during a fall event.

The term "pulse stimulation protocol" may refer to an ordered sequence of electrical pulses with particular characteristics targeting at least one target muscle group of the body. A pulse stimulation protocol may be correlated with (e.g., based at least in part on) characteristics of a fall such as an acceleration rate, direction of fall and/or the like. Each electrical pulse may be defined by one or more characteristics (i.e., electrical pulse characteristics) including, without limitation, intensity (e.g., defined by amplitude, voltage and/or current characteristics), duration (e.g., pulse duration), wave type and/or wave form (e.g., rectangular, triangular, square, sawtooth and the like). In some embodiments, a pulse stimulation protocol may target one or more muscles in at least one target muscle group. In various embodiments, a pulse stimulation protocol may be delivered to the at least one target muscle group via electrode(s) positioned adjacent the at least one target muscle group. Multiple pulse stimulation protocols may be applied simultaneously or in sequence (the sequence and/or duration of spacing between pulses applied according to multiple pulse stimulation protocols may be determined based at least in part on a controller as discussed herein). For example, a first pulse stimulation protocol may be applicable to a first plurality of electrodes collectively configured to stimulate muscles within a first target muscle group, and a second pulse stimulation protocol may be applicable to a second plurality of electrodes collectively configured to stimulate muscles within a second target muscle group. Accordingly, to stabilize a user's body, the wearable device may stimulate muscles within a plurality of target muscle groups each utilizing a different pulse stimulation protocol.

In various embodiments, one or more sequences of electrical pulses with particular electrical pulse characteristics may be provided to contract a certain muscle and/or target muscle group(s) based at least in part on a detected body position and/or body movement. For example, in order to contract the erector spinae muscle, an electrical pulse with a current between 20 mA and 40 mA may be required, whereas in order to contract the multifidus muscle, a current between 32 mA and 60 mA may be required, a current to contract a transfer abdominous muscle group may be between 25 mA to 45 mA, and a current to contract a gluteal muscle group may be between 14 mA to 34 mA. Additionally, electrical pulse characteristics required to contract a muscle or target muscle group may correspond with one or more additional user characteristics including muscle condition, age, weight, height, and/or the like. For example, a person with diastasis rectus abdominis (separation of abdominal muscles) or an elderly person with weak muscles may require more intense electrical pulses in order to contract his or her abdominal muscles. One or more sequences of electrical pulses targeting at least one muscle associated with at least one target muscle group may define a pulse stimulation protocol. In various embodiments, a sequence of various electrical pulses may be delivered to one or more muscles associated with a target muscle group or to a plurality of muscles associated with more than one target muscle group.

The term "user profile information/data" may refer to physiological information/data, biometric information/data, accelerometer information/data, location information/data (e.g., which may be utilized to correlate a location to a user's typical body movement pattern at that location, such as movement patterns while the user is at a workout facility, movement patterns while the user is located at home, and/or the like), time information/data and/or the like. User profile information/data may be collected and/or generated by one or more sensors associated with the user, such as sensors within a mobile device, sensors within a wearable device, sensors associated with one or more devices commonly used by the user (e.g., a glucose monitoring device), and/or the like. In certain embodiments, the user profile information/data may include muscle condition data, heart rate data, oxygen saturation data, pulse rate data, body temperature data, breath rate data, perspiration data, blink rate data, blood pressure data, neural activity data, cardiovascular data, pulmonary data, and/or various other types of information/data.

The term "body" may refer to a user's physical form, and the term may specifically be utilized to refer to a portion of a user's body, including at least a portion of one or more internal and/or external organs of a user. In general, the terms user, patient, wearer, individual, person and/or similar words are used herein interchangeably. Organs include, for example without limitation, the lungs, the heart, the kidneys, the bladder, the stomach, the intestines, the skin and the brain.

The term "electronically coupled" or "in electronic communication with" may refer to two or more electrical elements (for example, but not limited to, an example processing circuitry, communication module, input/output module memory, pulse wave generator, electrodes) and/or electric circuit(s) being connected through wired means (for example but not limited to, conductive wires or traces) and/or wireless means (for example but not limited to, wireless network, electromagnetic field), such that data and/or information (for example, electronic indications, signals) may be transmitted to and/or received from the electrical elements and/or electric circuit(s) that are electronically coupled.

III. COMPUTER PROGRAM PRODUCTS, METHODS, AND COMPUTING DEVICES

Embodiments of the present disclosure may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In some embodiments, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In some embodiments, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SWIM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 provides an example system architecture 100 that can be used in conjunction with various embodiments of the present disclosure. As shown in FIG. 1, the system architecture 100 may comprise one or more management computing entities 10, one or more user computing entities 20, one or more networks 30, one or more wearable devices 40 and/or the like. Each of the components of the system may be in electronic communication with, for example, one another over the same or different wireless or wired networks 30 including, for example, a wired or wireless Personal Area Network (PAN), Local Area Network (LAN), Metropolitan Area Network (MAN), Wide Area Network (WAN), and/or the like. Additionally, while FIG. 1 illustrates certain system devices as separate, standalone devices, the various embodiments are not limited to this particular architecture.

Exemplary Management Computing Entity

FIG. 2 provides a schematic of a management computing entity 10 according to some embodiments of the present disclosure. In general, the terms computing device, entity, device, system, and/or similar words used herein interchangeably may refer to, for example, one or more computers, computing devices, computing entities, desktop computers, mobile phones, tablets, phablets, notebooks, laptops, distributed systems, terminals, servers or server networks, blades, gateways, switches, processing devices, set-top boxes, relays, routers, network access points, base stations, the like, and/or any combination of devices adapted to perform the functions, operations, and/or processes described herein. Such functions, operations, and/or processes may include, for example, transmitting, receiving, operating on, processing, displaying, storing, determining, generating/creating, monitoring, evaluating, comparing, and/or similar terms used herein interchangeably. In some embodiments, these functions, operations, and/or processes can be performed on data, content, information, and/or similar terms used herein interchangeably.

As indicated, in some embodiments, the management computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like.

As shown in FIG. 2, In some embodiments, the management computing entity 10 may include or be in communication with one or more processing elements 205 (also referred to as processors, processing circuitry, and/or similar terms used herein interchangeably) that communicate with other elements within the management computing entity 10 via a bus, for example. As will be understood, the processing element 205 may be embodied in a number of different ways. For example, the processing element 205 may be embodied as one or more complex programmable logic devices (CPLDs), microprocessors, multi-core processors, coprocessing devices, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In some embodiments, the management computing entity 10 may further include or be in communication with non-volatile media (also referred to as non-volatile storage, memory, memory storage, memory circuitry and/or similar terms used herein interchangeably). In some embodiments, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In some embodiments, the management computing entity 10 may further include or be in communication with volatile media (also referred to as volatile storage, memory, memory storage, memory circuitry and/or similar terms used herein interchangeably). In some embodiments, the volatile storage or memory may also include one or more volatile storage or memory media 215 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the management computing entity 10 with the assistance of the processing element 205 and the operating system.

As indicated, in some embodiments, the management computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, management computing entity 10 may be configured to communicate via wireless external communication networks using any of a variety of protocols, such as general packet radio service (GPRS), Universal Mobile Telecommunications System (UMTS), Code Division Multiple Access 200 (CDMA200), CDMA200 1X (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), IR protocols, NFC protocols, RFID protocols, IR protocols, ZigBee protocols, Z-Wave protocols, 6LoWPAN protocols, Wibree, Bluetooth protocols, wireless universal serial bus (USB) protocols, and/or any other wireless protocol. The management computing entity 10 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the management computing entity's components may be located remotely from other management computing entity 10 components, such as in a distributed system. Furthermore, one or more of the components may be aggregated and additional components performing functions described herein may be included in the management computing entity 10. Thus, the management computing entity 10 can be adapted to accommodate a variety of needs and circumstances, such as including various components described with regard to a mobile application executing on the user computing entity 20, including various input/output interfaces.

Exemplary User Computing Entity

The user computing entity 20 may be in communication with the management computing entity 10 and the wearable device 40. The user computing entity 20 may obtain and provide (e.g., transmit/send) data objects describing raw data (e.g., sensor data and/or physiological data associated with the user) obtained by one or more additional sensors or sensing devices, captured by another user computing entity 20 or device and/or provided by another computing entity. The user computing entity 20 may be configured to provide (e.g., transmit, send) data objects describing at least a portion of the sensor data and/or physiological data to the management computing entity 10. Additionally, in various embodiments, a remote computing entity may provide data objects describing user information/data to the management computing entity 10. In some embodiments, a user (e.g., wearer) of the wearable device 40 may operate the wearable device 40 via the display 316 or keypad 318 of the user computing entity 20.

FIG. 3 provides an illustrative schematic representative of user computing entity 20 that can be used in conjunction with embodiments of the present disclosure. In various embodiments, the user computing entity 20 may be or comprise one or more mobile devices in certain embodiments. For example, a user computing entity 20 may be embodied as a user's mobile device, carried by the user, and therefore the user computing entity 20 may be in close proximity to a wearable device worn by the user, such that close-range wireless communication technologies may be utilized for communicating between a controller of a wearable device and the user computing entity 20.

As shown in FIG. 3, a user computing entity 20 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various devices, such as a management computing entity 10, another user computing entity 20, and/or the like. In an example embodiment, the transmitter 304 and/or receiver 306 are configured to communicate via one or more SRC protocols. For example, the transmitter 304 and/or receiver 306 may be configured to transmit and/or receive information/data, transmissions, and/or the like of at least one of Bluetooth protocols, low energy Bluetooth protocols, NFC protocols, RFID protocols, IR protocols, Wi-Fi protocols, ZigBee protocols, Z-Wave protocols, 6LoWPAN protocols, and/or other short range communication protocol. In various embodiments, the antenna 312, transmitter 304, and receiver 306 may be configured to communicate via one or more long range protocols, such as GPRS, UMTS, CDMA200, 1×RTT, WCDMA, GSM, EDGE, TD-SCDMA, LTE, E-UTRAN, EVDO, HSPA, HSDPA, Wi-Fi, Wi-Fi Direct, WiMAX, and/or the like. The user computing entity 20 may also include one or more network and/or communications interfaces 320 for communicating with various computing entities, such as by communicating data, content, information, and/or similar terms used herein interchangeably that can be transmitted, received, operated on, processed, displayed, stored, and/or the like.

In this regard, the user computing entity 20 may be capable of operating with one or more air interface standards, communication protocols, modulation types, and access types. More particularly, the user computing entity 20 may operate in accordance with any of a number of wireless communication standards and protocols. In a particular embodiment, the user computing entity 20 may operate in accordance with multiple wireless communication standards and protocols, such as GPRS, UMTS, CDMA200, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 20 can communicate with various other devices using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 20 can also download changes, add-ons, and updates, for instance, to its firmware, software (e.g., including executable instructions, applications, program modules), and operating system.

According to some embodiments, the user computing entity 20 may include location determining aspects, devices, modules, functionalities, and/or similar words used herein interchangeably to acquire location information/data regularly, continuously, or in response to certain triggers. For example, the user computing entity 20 may include outdoor positioning aspects, such as a location module adapted to acquire, for example, latitude, longitude, altitude, geocode, course, direction, heading, speed, UTC, date, and/or various other information/data. In some embodiments, the location module can acquire information/data, sometimes known as ephemeris information/data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the apparatus's 30 position in connection with a variety of other systems, including cellular towers, Wi-Fi access points, and/or the like. Similarly, the user computing entity 20 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The user computing entity 20 may also comprise a user interface device comprising one or more user input/output interfaces (e.g., a display 316 and/or speaker/speaker driver coupled to a processing element 308 and a touch interface, keyboard, mouse, and/or microphone coupled to a processing element 308). For example, the user interface may be configured to provide a mobile application, browser, interactive user interface, dashboard, webpage, and/or similar words used herein interchangeably executing on and/or accessible via the user computing entity 20 to cause display or audible presentation of information/data and for user interaction therewith via one or more user input interfaces. Moreover, the user interface can comprise or be in communication with any of a number of devices allowing the user computing entity 20 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 20 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 20 can capture, collect, store information/data, user interaction/input, and/or the like.

The user computing entity 20 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, information/data, applications, programs, program modules, scripts, source code, object code, byte code, compiled code, interpreted code, machine code, executable instructions, and/or the like to implement the functions of the user computing entity 20.

Exemplary Wearable Device

As noted above, the wearable device 40 may comprise or be an article or garment configured to fit closely to a wearer's body. In the embodiments discussed in detail herein, the wearable device is embodied as a belt wearable around a user's waist such that included electrodes are positioned proximate to target muscle groups discussed herein such that those electrodes are capable of stimulating the target muscle groups through electrical pulses. However, the wearable device 40 may alternatively be embodied as, for example and without limitation, a jacket, vest, shirt, pants, shorts, underwear, and/or the like. Such alternative configurations may additionally comprise electrodes positioned adjacent the same target muscle groups as discussed in reference to the belt configurations discussed herein. In various embodiments, the wearable device 40 is configured to (e.g., with an included sensor) monitor a user's COG and receive and transmit data/information (e.g., data objects) from the wearable device 40. A user's COG may be a reference location (e.g., point, center line and/or the like) at which the weight of the body (e.g., torso) can be considered to be concentrated with respect to a base of support (e.g., the feet). In order to remain upright while in a standing position, a balance between gravity pulling the body (e.g., torso) downward and the reaction force from the floor upward through the base of support (e.g., feet) which counteracts gravity is required. Muscles of the body also act to maintain a steady COG with respect to the body's base of support. Various muscles may contract in response to forces acting a person's body and/or a shift in the body's COG in order to adjust (e.g., shift, restore or the like) the COG and remain in balance.

In various embodiments, the wearable device 40 comprises a controller 404 (e.g., computing device, one or more computer processors) having a wireless communication transceiver and/or the like. The controller 404 may be integrated into the wearable device 40 (e.g., article or garment) and may be in wired or wireless communication with sensors 401 of the wearable device 40, the power supply of the wearable device, and/or the electrical pulse generation aspects of the wearable device 40. Accordingly, the controller 404 of the wearable device may be configured to (e.g., alone or together with the management computing entity 65) provide appropriate signals to elements of the wearable device 40 to stabilize the user and thereby prevent the user from falling. In some embodiments, the controller 404 may be in wireless communication with, but physically distinct from, the wearable device 40 (e.g., via short-range wireless communication, such as Bluetooth, via long-range wireless communication, and/or the like), which may encompass a wireless receiver without processing capability in such instances, thereby enabling appropriate signals to be passed to electrodes of the wearable device 40 as discussed herein. In certain embodiments, the controller 404 may comprise a user interface device (not shown) comprising one or more user input/output interfaces (e.g., a button, display and/or speaker/speaker driver coupled to a processing element and/or controller/processor and a touch interface, and/or microphone coupled to a processing element and/or controller). For example, the user interface may be configured to cause display or audible presentation of information/data and for user interaction therewith via one or more user input interfaces. The controller 404 may store instructions/parameters required for various operations by the wearable device 40. In various embodiments, the controller 404 of the wearable device 40 may comprise components similar the user computing entity 20 depicted in FIG. 3.

FIGS. 4A and 4B are schematics illustrating an example configuration of a wearable device 40. As shown, FIG. 4A depicts an inner portion of the example wearable device 40 that is configured to be worn adjacent an anterior portion of a user's body and FIG. 4B depicts an external (e.g., outer) portion of the example wearable device 40. As shown, the example wearable device 40 is embodied as a belt configured to fit closely to at least a portion of a user's abdomen and torso. In the illustrated embodiment, the belt comprises an elongated webbing extending along a length of the belt between a first end and a second end. The webbing is configured to wrap around the user's body to secure the wearable device 40 onto the user's body. The webbing may be an elastic material such that the wearable device 40 may be placed under tension when worn, such that additional included aspects (e.g., sensors, electrodes, and/or the like) may remain tightly placed against the user's body during normal movement of the user (e.g., twisting, sitting, standing, walking, running, and/or the like). However, in other embodiments, the webbing may be an inelastic material (e.g., a leather, an inelastic nylon, and/or the like). Moreover, the belt may comprise components of a fastening mechanism (e.g., hook-and-loop fasteners, a buckle, and/or the like) at opposing ends of the belt, thereby enabling opposing ends of the belt to be secured relative to one another to create a loop when secured around the user's body. When the fastening mechanism is secure and the belt is in a loop configuration, the belt defines a first, interior surface 400 (e.g., the belt surface to be placed against the user's body when worn) and an opposite second, exterior surface (e.g., the belt surface facing away from the user's body when worn).

As depicted in FIGS. 4A and 4B, the example wearable device 40 comprises at least one sensor 401 configured to monitor a user's COG and to generate COG data indicative of the user's current COG (e.g., generated in real-time). The at least one sensor may be positioned at least partially on an interior surface of the wearable device 40. In certain embodiments, the at least one sensor 401 is configured for receiving and/or capturing biometric inputs and/or information/data (e.g., regularly, continuously, and/or in response to certain triggers). For example, the wearable device 40 may comprise at least one sensor 401 configured to capture raw user sensor data. In some embodiments, the wearable device 40 may comprise microelectromechanical (MEMS) components, biological and chemical sensing components, electrocardiogram (ECG) components, electromyogram (EMG) components, electroencephalogram (EEG)-based neural sensing components, optical sensing components, electrical sensing components, sound components, vibration sensing components, accelerometer(s), pressure sensor(s) and/or the like. In certain embodiments, the at least one sensor may comprise a plurality of sensors of various sensor types so as to capture multiple types of COG data. In certain embodiments, COG data from one or more sensors (e.g., an accelerometer) may be analyzed (e.g., locally by the controller of the wearable device or via the management computing entity) to determine a user's COG based at least in part on detected movements of the user. Through such components various types of physiological information/data can be captured—such as body position and/or movement data/information, heart rate information/data, oxygen saturation information/data, body temperature information/data, breath rate information/data, perspiration information/data, neural information/data, cardiovascular sounds information/data, pulmonary sounds information/data, and/or various other types of information/data. The one or more sensors 401 of the wearable device 40 may be in electronic communication with the controller of the wearable device 40 such that it can exchange information/data (e.g., receive and transmit data) with the wearable device 40.

In certain embodiments, the controller 404 of the wearable device 40 may be configured to locally execute various algorithms on at least a portion of the raw and/or processed information/data obtained by the wearable device 40. For example, the controller of the wearable device 40 may be configured to determine a user's current COG (e.g., together with onboard sensors). In other embodiments, the controller 404 of the wearable device 40 transmits data objects describing at least a portion of the raw and/or processed information/data for processing by the management computing entity 10. As a part of processing the raw data received from the one or more sensors, the controller 404 of the wearable device 40 may be configured to receive data objects describing additional information (e.g., physiological data) from a user computing entity 20 and/or from the management computing entity 10, as such additional information may be utilized for determining appropriate control signals to be utilized to stabilize the user and thereby prevent the user from falling. In some embodiments, the controller 404 of the wearable device 40 may be configured to transmit (periodically or on request) data objects describing at least a portion of the raw data to the management computing entity 10 for processing. The controller 404 of the wearable device 40 may be configured to obtain (e.g., request and receive), a user profile data object comprising the baseline COG profile and pulse stimulation protocols from the management computing entity 10 and store the user profile data object. The controller 404 of the wearable device 40 may cause the at least one plurality of electrodes to provide (e.g., deliver) one or more pulses corresponding with at least one pulse stimulation protocol based at least in part on a determination that the user's COG satisfies particular criteria associated with providing the pulse stimulation protocol.

Moreover, the example wearable device 40 comprises a power source 411 (e.g., one or more batteries) to provide power to the onboard controller 404 to provide power to an electrical pulse generator 406 and one or more electrodes. The electrical pulse generator 406 operates together with at least a first plurality of electrodes 403, a second plurality of electrodes 405, a third plurality of electrodes 407 and a fourth plurality of electrodes 409 to provide electrical pulses to the user (e.g., to specific target muscle groups) to cause activation of those target muscle groups. The orientation of each of the electrodes 403-409 within the wearable device 40 is provided to align a respective electrode with a particular target muscle group. As a non-limiting example, a first plurality of electrodes 403 may be positioned proximate a first end of a belt (near a portion of the fastening mechanism) such that, when the belt is worn, the first plurality of electrodes 403 are positioned against a portion of the user's body that electrical pulses generated by the first plurality of electrodes 403 cause activation of one or more muscles within an abdominal muscle group. As a non-limiting example, the first plurality of electrodes 403 may be positioned adjacent to the abdominal muscle group when the belt is worn. The second plurality of electrodes 405, the third plurality of electrodes 407, and the fourth plurality of electrodes 409, respectively, are additionally positioned within the wearable device 40 so as to enable activation of specific target muscle groups when worn by the user. It should be understood that the electrodes may be positioned on an interior surface 400 of the wearable device (or at least a surface of the electrodes configured for delivering the electrical pulses may be positioned on an interior surface of the wearable device). Moreover, the electrodes may be configured such that direct contact between the electrodes and the user's skin does not result in damage to the user's skin. The electrodes may additionally be configured to deliver sufficient electrical pulses to be delivered through a shirt or other intermediate layer that may be worn between the wearable device and the user's skin.

As further illustrated, the interior portion 400 of the wearable device comprises a plurality of electrodes (e.g., which may be arranged into a plurality of discrete electrode groups located at discrete locations within the wearable device). An electrode may be an electrical device/conductor configured to apply electrical pulses to a user's body—specifically, to target muscles by applying an electrical pulse that travels through a user's skin to the underlying musculature. Each plurality of electrodes 403, 405, 407, 409 may comprise an array of electrodes. Each of the plurality of electrodes 403, 405, 407, 409 may be attached to the wearable device 40 or otherwise integrated at least partially within the interior surface 400 of the wearable device. The wearable device 40 (via the controller) may be configured to cause at least one of the plurality of electrodes 403, 405, 407, 409 to deliver one or more electrical pulses to a target area (e.g., target muscle(s)) of the user's body. Each of the plurality of electrodes 403, 405, 407, 409 may be associated with a unique identifier and/or control element corresponding with a location within the wearable device 40 such that each plurality of electrodes and/or one or more individual electrodes can be individually controlled by the wearable device 40. In various embodiments, each of the plurality of electrodes 403, 405, 407, 409 is in electronic communication with the wearable device 40 such that it can exchange information/data (e.g., receive and transmit data, data objects and the like) with the wearable device 40 controller/processor. Each of the plurality of electrodes 403, 405, 407, 409 may be associated with a particular area of the body (e.g., target muscle group). A target muscle group may comprise one or more muscles associated with an area of the body that acts to maintain a steady COG with respect to a person's base of support. In response to a shift in the body's COG, one or more muscles within a particular target muscle group may contract in order to restore balance and prevent the person from falling.

As mentioned, the electrodes of the wearable device 40 are configured to provide electrical pulses to particular target muscle groups so as to activate those muscle groups and to prevent the user from falling. FIGS. 8A and 8B provide example schematics of an anterior body 800A and posterior body 800B of a user depicting various areas of the user's body, including example locations of certain target muscle groups to be targeted via certain embodiments.

Referring to FIG. 8A, as shown, the body 800A comprises a right abdominal body area 801 and a left abdominal body area 803. The right abdominal body area 801 may be associated with one or more abdominal muscles on a right side of the body defining a target muscle group. For example, a target muscle group of the right abdominal body area 801 may include right internal oblique, right external oblique, right transverse abdominis and right rectus abdominis muscles. Similarly, the left abdominal body area 803 may be associated with one or more abdominal muscles on a left side of the body defining a target muscle group. For example, an example target muscle group of the left abdominal body area 803 may include left internal oblique, left external oblique, left transverse abdominis and left rectus abdominis muscles. In certain embodiments, a plurality of electrodes may be positioned within the wearable device so as to activate muscle groups within the left abdominal body area 803 and/or the right abdominal body area 801 when the wearable device 40 is worn by a user.

Referring to FIG. 8B, as shown, the body 800B comprises a back body area 805, a left gluteal body area 807, and a right gluteal body area 809. The back body area 805 may be associated with one or more back muscles on a posterior side of the body defining a target muscle group. For example, an example target muscle group of the back body area 805 may include erector spine (e.g., spinalis, longissimus and/or iliocostalis) muscles. The left gluteal body area 807 may be associated with one or more gluteal muscles on a posterior side of the body defining a target muscle group. For example, an example target muscle group of the left gluteal body area 807 may include left gluteus maximus, left gluteus medius and left gluteus minimus muscles. The right gluteal body area 809 may be associated with one or more gluteal muscles on a posterior side of the body defining a target muscle group. For example, an example target muscle group of the right gluteal body area 809 may include right gluteus maximus, right gluteus medius and right gluteus minimus muscles. Characteristics of the muscle contractions corresponding with a particular target muscle group may vary in response to the incident COG change (e.g., shift). For example, in response to forward movement (anterior flexion) occurring on a left side of a body, one or more muscles in one or more target muscle groups may contract (e.g., a target muscle group associated with a left abdominal body area 803 and/or a left gluteal body area 807 may contract). In response to forward movement occurring on a right side of a body, one or more muscles in one or more target muscle groups may contract (e.g., a target muscle group associated with a right abdominal body area 801 and/or a right gluteal body area 809 may contract). In response to centralized forward movement, one or more muscles in target muscle group associated with the back body area 805 may contract.

By way of example, in relation to FIG. 4A, the first plurality of electrodes 403 may be positioned within the wearable device 40 so as to be associated with the left abdominal body area 803 when the wearable device 40 is worn by the user so as to provide electrical pulses to the left abdominal area 803, the second plurality of electrodes 405 may be positioned within the wearable device 40 so as to be associated with a back body area 805 when the wearable device 40 is worn by the user so as to provide electrical pulses to the back body area 805, the third plurality of electrodes 407 may be positioned within the wearable device 40 so as to be associated with the right gluteal body area 809, and left gluteal body area 807 when the wearable device 40 is worn by the user so as to provide electrical pluses to the right gluteal body area 809 and the left gluteal body area 807, and the fourth plurality of electrodes 409 may be positioned within the wearable device 40 so as to be associated with the right abdominal body area 801 when the wearable device 40 is worn by the user so as to provide electrical pulses to the right abdominal body area 801.

Referring to FIG. 4B, a schematic of an example exterior surface 402 of the wearable device 40 of FIG. 4A is shown. As depicted, the exterior surface 402 of the wearable device 40 defines an outer side of the wearable device 40 and comprises the controller 404 and an electrical pulse generator 406. However it should be understood that such elements may be positioned elsewhere, such as within an interior surface of the wearable device 40.

As discussed herein, the controller 404 may comprise one or more control elements for transmitting a control signal to control (e.g., adjust or modify) various operations and operational parameters of the wearable device 40. For example, the user may control (e.g., override) the wearable device 40 such as in order to adjust characteristics of or stop delivery of the one or more electrical pulses via the controller 404 of the wearable device 40. In another example, a user may transmit a control signal to adjust electrical pulse characteristics (e.g., increase intensity, reduce intensity, sustain contraction or the like).

Moreover, the controller 404 of certain embodiments additionally comprises an emergency assistance call system (e.g., comprising a user interface element, such as a button, a transmitter for sending an emergency assistance signal to an external system, and/or the like) that is configured to call for emergency assistance (e.g., an ambulance) upon the occurrence of certain trigger events. For example, the emergency assistance call system may be configured to call for emergency assistance upon the user interacting with the included user interface element. In other embodiments, the emergency assistance call system may integrate with the various sensors discussed above, and may be configured to automatically call for emergency assistance upon the controller 404 sensing the user has fallen.

In various embodiments, the electrical pulse generator 406 may comprise an electrical device and/or circuit configured to generate electrical pulses with particular characteristics and cause delivery of the electrical pulses via one or more electrodes (e.g., at least one plurality of electrodes 403, 405, 407, 409). The electrical pulse generator 406 may be in electronic communication with the controller 404 of the wearable device 40 and each plurality of electrodes 403, 405, 407, 409 such that it receives control signals from the controller 404 of the wearable device 40 and the various electrodes of the wearable device 40 (e.g., transmit a control signal to at least one plurality of electrodes 403, 405, 407, 409).

V. EXEMPLARY OPERATION

FIGS. 6 and 7, 8 and 9 are flowcharts illustrating example steps, processes, procedures, and/or operations; and FIGS. 10 and 11 provide operational examples.

Although the following exemplary operations are described as being performed by one of the wearable device 40 (e.g., via the controller 404), the management computing entity 10 or the user computing entity 20, it should be understood that in various embodiments, the operations can be interchangeably performed by other components within the system architecture 100.

Various embodiments may be configured to utilize one or more user profiles (e.g., a user-specific COG profile) to facilitate operation of the wearable device 40. The user-specific COG profiles may comprise data indicative of characteristics of the user (e.g., data indicative of the user's age, gender, medical conditions, and/or the like, which may be obtained from electronic medical record (EMR) data stored in a data storage area and associated with the user), as well as data indicative of functional results of operation of the wearable device (e.g., data indicating that a particular electrical pulse level was/was not sufficient to prevent a fall under particular operation conditions determined at least in part on the operation of the sensors of the wearable device 40. Accordingly, the management computing entity 10 may be configured to obtain (e.g., receive) and process data objects describing raw data (sensor data, physiological data, user profile information/data and/or the like) associated with a user in order to generate a baseline COG profile. An example baseline COG profile may define a plurality of threshold COG offset values. Each COG offset value may correspond with a particular body position, a body movement, and/or a direction of body movement for the user. The baseline COG profile may be stored in conjunction with or otherwise associated with a user profile data object. The management computing entity 10 may be configured to generate or identify, based at least in part on the baseline COG profile and user profile information, a plurality of pulse stimulation protocols each corresponding with at least one threshold COG offset value and a corresponding body position and/or body movement for the user. The pulse stimulation protocols and baseline COG profile may be stored in conjunction with or otherwise associated with the user profile data object. In some embodiments, an operator (e.g., clinician) interfacing with the management computing entity 10 may modify the baseline COG profile and/or pulse stimulation protocols associated with the user profile data object. The management computing entity 10 may be configured to store and/or in turn provide (e.g., send, transmit) a user profile data object comprising the baseline COG profile and the stored pulse stimulation protocols to the wearable device 40. The management computing entity 10 may be configured to obtain (e.g., receive, request) and process a data object describing raw data (e.g., sensor data) collected by sensors of the wearable device 40 and/or other sensors and sensing devices associated with the user in order to update the baseline COG profile and the stored pulse stimulation protocols for the user. The management computing entity 10 may be configured to process (periodically or in response to receiving) additional data/information associated with the user in order to update (e.g., adjust, change) the baseline COG profile and/or stored pulse stimulation protocols for the user. The management computing entity 10 may periodically provide (e.g., send, transmit) an updated user profile data object comprising the most up-to-date baseline COG profile and pulse stimulation protocols to the wearable device 40. The management computing entity 10 may generate a user interface data object corresponding with the user profile data object and provide (e.g., transmit, send) the user interface data object to one or more user computing entities 20 or other computing entities for presentation (e.g., operated by the user, clinicians and/or the like).

Fall Detection and Prevention

In various embodiments, an example wearable device 40 may be configured to monitor and or determine a user's COG. As noted above, a user's COG may be a reference location (e.g., point, center line and/or the like) at which the weight of the body (e.g., torso) can be considered to be concentrated with respect to a base of support (e.g., the feet). In various embodiments, a wearable device 40 may be configured to store a baseline COG profile defining a plurality of threshold COG offset values. The threshold COG offset values may be utilized as determining whether the user is off-balance (and may indicate a direction in which the user is off-balance) so as to determine whether the wearable device 40 should be utilized to provide an electrical pulse to a particular target muscle group to activate the particular target muscle group to stabilize the user and thereby assist in regaining the user's balance. The COG profile may differ between individual users, such that COG threshold values may be different based on the unique characteristics of each individual user. The wearable device 40 may be configured to determine whether COG data collected in real-time from the one or more sensors satisfies a COG threshold for the user. In response to determining that the COG data for the user satisfies a COG threshold, the wearable device 40 may identify one or more pulse stimulation protocols for at least one plurality of electrodes. An example pulse stimulation protocol may comprise at least one of a first electric current level (e.g., in mA), a first pulse duration, and/or a first electrical pulse wave type to be generated by the first plurality of electrodes. In response to identifying the pulse stimulation protocol, the wearable device 40 may cause the respective plurality of electrodes to provide one or more electrical pulses corresponding to the pulse stimulation protocol.

Determining whether a COG threshold is violated for a particular user may be based at least in part on characteristics of the user, characteristics of the user's current activity, data indicative of the user's current location, and/or the like. FIG. 5 provides an example schematic 500 illustrating a person's current COG in a plurality of body positions and/or body movements to illustrate differences in a user's COG for various body positions and activities. A first illustration 501 depicts a current COG for a person in an upright position. As depicted, the person's current COG is a reference point and/or centerline located around the person's torso. As illustrated, the user in the first illustration 501 is maintaining a steady COG with respect to his or her base of support (e.g., feet). A second illustration 503 depicts a current COG for a person while walking. As depicted, the person's current COG is a reference point and/or centerline that is also located around the person's torso, but is further away from the body centerline in comparison to the user's COG in the first illustration 501. The user in the second illustration 503 is also maintaining a steady COG with respect to his or her base of support (e.g., feet). A third illustration 505 depicts a current COG for a person that is falling. As depicted, the person's current COG is not aligned with the body centerline and is located outside of the base of support. Accordingly, the person is failing to maintain a steady COG with respect to his or her base of support (e.g., feet). As discussed herein, when a user is detected to be falling, the wearable device 40 is configured to provide one or more electrical pulses to contract specific target muscles to assist the user in regaining his/her balance.

FIG. 6 is a flowchart diagram illustrating an example process 600 by a management computing entity 10, in accordance with some embodiments of the present disclosure.

Beginning at step/operation 601, management computing entity 10 obtains a user profile data object describing user information/data. In some embodiments, the user profile data object may be provided by a remote computing entity (e.g., a remote computing entity storing user EMR data). The user profile data object may describe various types of information associated with a particular user including, but not limited to, age, gender, weight, height, body mass index (BMI), weight distribution and/or the like. In some embodiments, user profile data objects describing user information may be provided by one or more computing entities, one or more other wearable or health management devices (e.g., fitness trackers), a mobile device and/or the like. In some embodiments, step/operation 601 may be performed as part of registering a user. For example, a user profile data object for a user may be generated/created as part of registration. However, as will be recognized, a user profile may already exist and be stored in a user profile database; in such a case, registration may simply link to an existing user profile. Each user profile may be identifiable via one or more identifiers (e.g., social security numbers, patient IDs, member IDs, participant IDs, usernames, globally unique identifiers (GUIDs), universally unique identifiers (UUIDs), and/or the like) configured to uniquely identify the user profile. As part of registering a user, management computing entity 10 may obtain (e.g., request and receive) various data objects describing information/data associated with a user. In various embodiments, management computing entity 10 receives one or more data objects describing the user information/data for generation/creation of and/or storage in conjunction with a user profile data object. In some embodiments, a user's EMR may be associated with and/or otherwise stored in conjunction with the user profile data object.

At step/operation 603, management computing entity 10 obtains a user sensor data object describing sensor data associated by the user. In some embodiments, the controller of the wearable device 40 may obtain (e.g., collect) user sensor data via one or more sensors 401 (e.g., accelerometers, pressure sensors, physiological sensors and/or the like) for an initial time period and generate and transmit a user sensor data object describing at least a portion of the obtained user sensor data to the management computing entity 10. The management computing entity 10 may store the user sensor data object in conjunction with the user profile data object.

At step/operation 605, based at least in part on the user profile information stored in a user profile data object and the user sensor data stored therewith, the management computing entity 10 generates a baseline COG profile for the user. In some embodiments, a baseline COG profile may define a plurality of threshold COG offset values in which each COG offset value is associated with a particular body movement and/or body position. As discussed above in relation to FIG. 6, a person's COG may vary depending on their current body position and/or body position. For example, a person's COG while standing upright may be different from the person's COG while walking such that the reference location (e.g., point, center line and/or the like) defining the COG is different for each respective body position and/or body movement. Accordingly, a COG offset value may be a predetermined (e.g., allowed, permissible or the like) offset value from a baseline or threshold COG value corresponding with a particular body position and/or body movement. The COG offset value may be a displacement value/amount such as a tilt, angle, distance and/or the like with respect to the baseline/threshold COG value. The COG offset value may be influenced by and determined based at least in part on additional user parameters (e.g., age, gender, body weight, height, muscle condition and/or the like). Accordingly, the management computing entity 10 may be configured to periodically update the baseline COG profile data as additional data for the user (e.g., changes in the user profile data object) are obtained so as to maintain an updated COG profile for the user. In general, when a person's COG offset value corresponding with a particular body position and/or body movement is exceeded, it is likely that the person will lose his or her balance and fall. In some embodiments, the wearable device 40 may be configured to determine the baseline COG profile for a user and provide (e.g., transmit, send) a baseline COG profile data object to the management computing entity 10.

At step/operation 607, the management computing entity 10 determines a plurality of pulse stimulation protocols corresponding with the determined baseline COG profile. A pulse stimulation protocol in accordance with certain embodiments defines characteristics of an electrical pulse (or series of electrical pulses) to be applied to the user's body (to specific target muscle groups) so as to cause certain of the user's muscles to contract to stabilize the user's body by assisting the user in regaining balance prior to a fall. The one or more pulse stimulation protocols may collectively define an ordered sequence of electrical pulses with particular characteristics targeting at least one target muscle of the body. An electrical pulse may be defined by one or more characteristics (i.e., electrical pulse characteristics) including, without limitation, intensity (e.g., defined by an electrical current, measured in milliamps), duration (e.g., pulse duration, measured in seconds), and/or wave form (e.g., defining how the electrical current is applied, such as a rectangular current wave, a triangular current wave, a square current wave, a sawtooth current wave, a sinusoidal current wave, and/or the like). In some embodiments, a pulse stimulation protocol may target one or more muscles in at least one target muscle group. In various embodiments, a pulse stimulation protocol may be delivered to the at least one target muscle group via at least one plurality of electrodes positioned adjacent the at least one target muscle group.

FIG. 9 is a tree diagram 900 depicting example pulse stimulation protocols, in accordance with some embodiments of the present disclosure. As illustrated each example pulse stimulation protocol may be provided as a part of a structured plurality of pulse stimulation protocols 902, 904, 906 comprising an ordered sequence of electrical pulses having certain electrical pulse characteristics to be applied to a respective target muscle(s) or target muscle group (e.g., as shown, each structured plurality of pulse stimulation protocols 902, 904, 906 targets erector spine, multifidus, transverse abdominis muscles and gluteal muscle group) in an order provided to maintain a user's balance by activating muscle groups in such a manner so as to facilitate a user regaining his/her balance (by moving the user's COG into alignment with the user's base of support). As depicted, the first example structured plurality of pulse stimulation protocols 902 corresponds with a forward COG shift (anterior flexion) occurring on a right side of a body. As depicted, the second example structured plurality of pulse stimulation protocols 904 corresponds with a center forward COG shift. As depicted, the third example structured plurality of pulse stimulation protocols 906 corresponds with a forward COG shift occurring on a left side of the body. In various embodiments, electrical pulse characteristics of an electrical pulse applied to a respective muscle and/or target muscle group may differ based at least in part on the corresponding type of COG shift. In various embodiments, stored pulse stimulation protocols may be modified and refined over time based on new data/information associated with the user, including user response to delivered pulses. In some embodiments, a user may manually adjust and/or override a pulse stimulation protocol (e.g., by providing user input to the management computing entity 10).

Returning to FIG. 6, at step/operation 609, the management computing entity 10 stores the baseline COG profile and corresponding pulse stimulation protocols in association with the user profile data object. As noted, the baseline COG profile for a user may be periodically updated (e.g., as new data is provided to a user's EMR, as the wearable device 40 is utilized to assist a user in regaining his/her balance through application of an electrical pulse protocol, and/or the like). Accordingly, the controller 404 may implement a feedback loop that updates the COG profile for a user based on a determined effectiveness of the application of an applied pulse stimulation protocol to assist a user in regaining his/her balance during a detected fall event. For example, the controller 404 (e.g., together with the management computing entity 10) may determine whether a particular electrical pulse intensity (e.g., current level), electrical pulse wave form, and/or other characteristics of the applied electrical pulse were effective to assist the user in regaining his/her balance. For example, the controller 404 may determine whether a higher current level should be applied to assist the user in regaining the user's balance, whether a lower current level should be applied to assist the user in regaining the user's balance without over-fatiguing the user's muscles, and/or the like.

Subsequent to storing the baseline COG profile and corresponding pulse stimulation protocols, at step/operation 611, the management computing entity provides (e.g., transmits, sends and/or the like) the user profile data object to the controller 404 of the wearable device 40 to enable application of a pulse stimulation protocol to maintain the user's balance during a fall event.

FIG. 7 is a flowchart diagram illustrating an example process 700 by the wearable device 40, in accordance with some embodiments of the present disclosure.

Beginning at step/operation 701, the controller 404 of the wearable device 40 may be configured to obtain (e.g., request, receive or the like) a stored user profile data object comprising a baseline COG profile and corresponding pulse stimulation protocols from the management computing entity. The controller 404 of the wearable device 40 may, in certain embodiments, receive an applicable stored user profile for a user based at least in part on user input received via a user interface of the wearable device 40 (or based on user input received from a user computing entity associated with the wearable device 40). It should be understood that an appropriate user profile may be identified via any of a variety of alternative mechanisms, such as by identifying a user profile associated with a particular user computing entity (e.g., the user profile of a designated owner of a user computing entity) that is within communication range of the wearable device 40. By receiving the user profile applicable to the particular user, baseline COG profiles and associated electrical pulse stimulation protocols are identified such that the user-specific electrical pulse stimulation protocols may be utilized for the user wearing the wearable device 40. In some embodiments, the wearable device 40 may request the user profile data object from the management computing entity 10. The controller of the wearable device 40 may periodically request an updated user profile data object relevant for the user wearing the wearable device 40 from the management computing entity. In some embodiments, the controller of the wearable device 40 may generate at least a portion of data stored within the user profile data object. In one example, the controller of the wearable device 40 may generate an initial user profile data object for a user based at least in part on evaluation of user sensor data collected via one or more sensors 401 of the wearable device 40 while the user is wearing the wearable device 40. In some embodiments, the wearable device 40 may determine initial operating parameters and/or generate a user baseline COG profile by monitoring the user (e.g., obtaining and analyzing sensor data collected via one or more sensors 401 of the wearable device 40 while the user moves through walking, standing, sitting, and/or other positions) for an initial time period. In some embodiments, the wearable device 40 may provide (e.g., transmit, send) a user sensor data object to the management computing entity 10 for generating and storing the user baseline COG profile within a data storage area associated with the management computing entity 10. Subsequent to receiving new information and/or periodically, the wearable device 40 or management computing entity 10 may update the user baseline COG profile stored in conjunction with a user profile data object and provide (e.g., transmit) an updated user profile data object periodically and/or on request.

Subsequent to obtaining a user profile data object at step/operation 701, at step/operation 703, the wearable device 40 monitors the user's COG. For example, the wearable device 40 may analyze at least a portion of user sensor data collected by one or more sensors 401 of the wearable device 40 in order to monitor changes to the user's COG in real-time. The wearable device 40 may store at least a portion of the user sensor data and/or results of the analysis in conjunction with the user profile data object. The wearable device 40 may store the user sensor data in association with sensor identifier information/data (e.g., metadata, timestamp data and/or the like).

At step/operation 705, based at least in part on monitoring the user's COG, the wearable device 40 detects a change in the user's COG. As described above, detecting a change in the user's COG may comprise detecting a COG value such as a displacement value/amount (e.g., a tilt, angle, distance and/or the like) that satisfies a threshold COG value (or differs from a baseline COG value by at least a threshold amount) corresponding with a current body position and/or body movement of the user.

Subsequent to detecting a change in the user's COG, at step/operation 707, the wearable device 40 determines whether the user COG data satisfies a threshold such that the user is likely to lose his or her balance and/or fall. For example, the wearable device 40 may determine that the current user COG value is within a defined range of or sufficiently close to a stored threshold value. The wearable device 40 may compare the current user COG value with a stored user threshold COG offset value corresponding with the user's current body position and/or body movement.

At step/operation 709, the wearable device 40 determines, based at least in part on whether the user COG data satisfies a threshold whether or not intervention by providing one or more electrical pulses to target muscle groups is required to maintain the user's balance and avoid falling over.

In response to determining that the current user COG value does not satisfy a threshold (i.e., the user is not likely to lose his or her balance and/or fall down), the wearable device proceeds to step/operation 715. At step/operation 715, the wearable device 40 updates the stored user profile data object based at least in part on data describing the detected change in the user's COG. In some embodiments, the wearable device 40 may modify or update (e.g., increase or decrease) a monitoring frequency based at least in part on low frequency of required interventions over a particular time period.

However, in response to determining that the current user COG value satisfies a threshold (i.e., the user is likely to lose his or her balance and/or fall down), the wearable device 40 proceeds to step/operation 711. At step/operation 711, the wearable device 40 identifies one or more pulse stimulation protocols (e.g., a structured plurality of pulse stimulation protocols) corresponding with the user's current COG and/or characteristics of the COG change/shift. As noted above, pulse stimulation protocols may be stored in conjunction with a user profile data object for the user.

At step/operation 713, the wearable device 40 causes delivery of electrical pulses according to the one or more pulse stimulation protocols in order to restore stability and prevent the user from falling. As noted above, the pulse stimulation protocol may be an ordered sequence of electrical pulses generated by the electrical pulse generator of the wearable device 40. The pulse stimulation protocol may be delivered via at least one plurality of electrodes 404, 405, 407, 409 in electronic communication with the electrical pulse generator 406 and the wearable device 40 based at least in part on control signals generated by the controller 404 of the wearable device 40. It should be understood that a structured plurality of pulse stimulation protocols may encompass a first pulse generated by a first plurality of electrodes, followed by a second pulse generated by a second plurality of electrodes. In certain embodiments, the first pulse may be characterized by a duration, intensity, and/or wave shape that differs from the second pulse, and each pulse may be generated based at least in part on determined pulse characteristics deemed effective for contracting muscles within a corresponding muscle group to prevent a fall event. In some embodiments, the wearable device 40 may cause delivery of more than one pulse stimulation protocol. In various embodiments, the wearable device 40 may dynamically modify (e.g., refine, adjust) the pulse stimulation protocol in real-time based at least in part on the user's response and/or user input. For example, the wearable device 40 may determine that based at least in part on data (e.g., historical) stored in conjunction with the user profile data object, the user's muscles are becoming fatigued, such that an electrical pulse is unlikely to cause contraction of the muscles. As a result, the wearable device 40 may deliver less intense stimulation protocol to avoid fatiguing the muscles, or may deliver a more intense stimulation protocol in instances in which contraction of the muscles is determined to be important for avoiding a fall event, regardless of the fatigue of the muscle. In certain embodiments, adjusting the intensity of a pulse stimulation protocol may be executed by modifying one or more characteristics of a pulse stimulation protocol (e.g., pulse duration, wave form type and/or the like). By way of example, if a pulse stimulation protocol indicates that pulses should be delivered with a 1 second gap therebetween and the wearable device 40 determines that the user's muscles are getting fatigued, the wearable device 40 may cause delivery of the pulses with a gap of 3 seconds instead. In some embodiments, the wearable device 40 may identify or modify electrical pulse characteristics based at least in part on characteristics of a detected fall (e.g., a detected frequency of COG shift, rate of acceleration associated with the fall and/or the like). For example, if a slow fall rate is detected, the wearable device 40 may cause delivery of sawtooth wave pulses. However, if a fast fall rate is detected, the wearable device 40 may cause delivery of rectangular wave pulses instead, which may ascend to a maximum current intensity at a faster rate and sustain a contraction for a longer period of time in comparison to sawtooth wave pulses. In another example, if a delivered sequence of pulses does not stabilize a user's COG within a target time period, the wearable device 40 may subsequently cause delivery of a different sequence of pulses (e.g., a sequence of pulses at a higher current, longer duration, shorter gap therebetween and/or the like). In general, combinations of different types of pulses (e.g., rectangular, sawtooth, trapezoid and/or the like) reduce the likelihood of muscle fatigue and increase the likelihood of restoring COG stability in comparison to delivery of a single type of pulse. Additionally, the wearable device 40 may account for additional safety considerations based at least in part on user characteristics (e.g., age, muscle condition, time since last intervention, user response data, user input and/or the like).

In certain embodiments, the controller 404 may be configured to implement a safety configuration in which no electrical pulses are to be provided to any of the user's target muscle groups during a particular period of time in which the user is determined to be fatigued. During this safety configuration, the controller 404 may be configured to provide information to the user (e.g., via a user interface) suggesting the user rest (e.g., by sitting) so as to minimize a fall risk. Because the user's target muscles are determined to be fatigued during the safety configuration, applying an electrical pulse to the user's target muscles would be unlikely to result in an adequate muscle contraction to prevent a fall, and therefore the system is configured to allow the target muscles to rest and recover for a period of time, such that a later electrical pulse would result in adequate muscle contraction to assist the user in preventing a fall.

Subsequent to causing delivery of the pulse stimulation protocol, at step/operation 715, the controller of the wearable device 40 updates the stored user profile data object based at least in part on data describing the intervention (e.g., delivered stimulation protocol(s)) and/or the user's response/input. By updating the stored user profile data object, the stored user profile data object may be maintained in a current state of data, reflecting a user's resiliency to fatigue, as well as the effectiveness of various pulse stimulation protocols in preventing falls by the user. Later pulse stimulation protocols may be adjusted to reflect current characteristics of the user, as reflected within the updated user profile data object.

Subsequent to updating the stored user profile data object, at step/operation 717, the controller of the wearable device 40 provides (e.g., transmits, sends) the updated user profile data object to management computing entity 10. However, it should be understood that in certain embodiments, updating the stored user profile data object may comprise the controller of the wearable device 40 providing updated data to the management computing entity 10, and the management computing entity 10 may update the stored user profile data object.

Returning to FIG. 6, at step/operation 613, management computing entity periodically obtains an updated user profile data object describing user information and/or sensor data obtained by controller of the wearable device 40 such as data describing COG data, intervention data, user response data and/or the like.

At step/operation 615, in response to receiving an updated user profile data object, the management computing entity 10 updates the baseline COG profile and/or pulse stimulation protocols for the user which are stored in conjunction with user profile data object. The management computing entity 10 may update the baseline COG profile and/or pulse stimulation protocols based at least in part on new user EMR data, sensor data provided by other computing entities and/or the like. In so doing, the management computing entity 10 can refine the outputs generated by the wearable device 40 over time and prevent muscle fatigue caused by over stimulation of the muscles. Additionally, the most effective pulse stimulation protocols for a particular user, and for particular fall scenarios can be identified over time. In certain embodiments, the management computing entity may be configured to refine one or more pulse stimulation protocols for a user via a machine-learning based model that utilize a training data set comprising data indicating a type of pulse applied to a particular user, as well as the result of the pulse. Such training data may additionally comprise additional data indicative of characteristics of a user to which a pulse was applied, thereby enabling selection of training data deemed relevant to a particular user (e.g., the user having characteristics similar to those of a particular training data set). Moreover, updated information based on new user characteristics (e.g., weight loss or weight gain, medical history including recent medical procedures and/or the like) can be provided for updating the baseline COG profile and/or stimulation profile, which may be further utilized to refine pulse stimulation protocols to be utilized for certain users. In some embodiments, the user computing entity 20 and/or one or more other computing devices may be are configured to obtain (e.g., monitor, detect, and/or the like) additional body data and provide data object(s) describing the body data. The body data may be or comprise physiological information/data, biometric information/data, accelerometer information/data, heart rate data, oxygen saturation data, pulse rate data, body temperature data, breath rate data, perspiration data, blood pressure data, neural activity data, cardiovascular data, pulmonary data, and/or various other types of information/data which may be relevant for updating the user profile data object storing the baseline COG profile and/or corresponding pulse stimulation protocols.

Subsequent to updating the user profile data object at step/operation 615, at step/operation 617, the management computing entity 10 transmits an updated user profile data object to the wearable device 40. In various embodiments, the management computing entity 10 and the wearable device 40 periodically update and provide (e.g., send, transmit) user profile data objects and in so doing effectively incorporate real-time user information and user profile information/data in continuous feedback loop.

Generating a User Interface Data Object

In various embodiments, a variety of sources (e.g., management computing entity 10) may provide (e.g., transmit, send) a mobile application for download and execution on a user computing entity 20 (e.g., in response to a request to download the mobile application generated at the user computing entity 20). In another embodiment, the mobile application may be pre-installed on the user computing entity 20. And in yet another embodiment, the mobile application may be a browser executing on the user computing entity 20. The mobile application may comprise computer-executable program code (e.g., a software application) that provides the functionality described herein. The mobile application may enable various functionalities as discussed herein. Moreover, although specifically referenced as a mobile application, it should be understood that the mobile application may be executable by any of a variety of computing entity types, such as desktop computers, laptop computers, mobile devices, and/or the like. In various embodiments, instructions may be automatically generated (e.g., by the management computing entity 10) or provided based at least in part in response to clinician input/instructions provided by a clinician interacting with the management computing entity 10. The instructions may comprise messages in the form of banners, headers, notifications, and/or the like.

In some embodiments, at least a portion of the obtained wearable device sensor data may be transferred to the user computing entity 20 and/or the management computing entity 10 for performing at least a portion of the required operations. The wearable device 40 or user computing entity 20 may be configured to provide information/data in response to requests/queries received from the management computing entity 10. In various embodiments, the wearable device 40 may be managed, calibrated and/or otherwise controlled at least in part by a management computing entity 10. The management computing entity 10 may generate a user interface data object based at least in part on a user profile data object and provide (e.g., transmit, send) the user interface data object to one or more client computing entities.

FIG. 10 provides an operational example of a user interface data object generated by the management computing entity 10. The management computing entity 10 may generate an alert or notification based at least in part on data/information stored in association with a user profile data object. The wearable device 40/management computing entity 10 may provide one or more data objects corresponding with the alert/notification for presentation by a user computing entity 20 (e.g., for dynamically updating a user interface 1002 of a user computing entity 20). In one example, as depicted, the user interface 1002 of the user computing entity 20 provides an alert indicating a number of falls prevented by the wearable device over a particular time period. As will be recognized, a variety of other approaches and techniques can be used to adapt to various needs and circumstances.

VI. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only, and not for purposes of limitation.

What is claimed is:

1. A wearable device comprising:
a webbing extending between a first end and a second end, wherein the first end and the second end comprise respective fastening components that interact to enable connection between the first end and the second end to secure the webbing around a waist of a user such that the webbing defines (i) an interior surface to be placed against a body of the user and (ii) an opposite exterior surface when the first end is connected with the second end;
a controller secured to the webbing;
one or more sensors in electronic communication with the controller, wherein the one or more sensors are secured to the webbing and configured to generate center of gravity (COG) data indicative of a balance of the user;
a first plurality of electrodes secured on the interior surface of the webbing, wherein (a) the first plurality of electrodes are (i) in electronic communication with the controller, and (ii) configured to cause delivery of electrical pulses in accordance with a first electrical pulse stimulation protocol responsive to a first signal from the controller, (b) the first signal is provided from the controller responsive to a determination that a fall event for the user is likely, and (c) the electrical pulses are configured to stimulate a first target muscle group of the user; and a second plurality of electrodes secured on the interior surface of the webbing, wherein (a) the second plurality of electrodes are (i) in electronic communication with the controller, and (ii) configured to cause delivery of electrical pulses in accordance with a second electrical pulse stimulation protocol responsive to a second signal from the controller, (b) the second signal is provided from the controller responsive to the determination that the fall event for the user is likely, and (c) the electrical pulses in accordance with the second electrical pulse stimulation protocol are configured to stimulate a second target muscle group of the user, wherein the controller is configured to modify the first electrical pulse stimulation protocol and the second electrical pulse stimulation protocol based at least in part on a muscle condition of the user.

2. The wearable device of claim 1, further comprising a third plurality of electrodes (i) secured on the interior surface of the webbing, (ii) in electronic communication with the controller' and (iii) configured to apply a third electrical pulse stimulation protocol configured to stimulate a third target muscle group of the user upon receipt of signals from the controller.

3. The wearable device of claim 1, wherein the controller is in electronic communication with a management computing entity storing baseline COG profiles for each of a plurality of users, and wherein the controller is configured to:
receive a baseline COG profile for the user wearing the wearable device, wherein the baseline COG profile defines at least one threshold COG offset value;
compare, in real-time, the COG data indicative of the balance of the user with the at least one threshold COG offset value of the baseline COG profile for the user; and
upon determining that the COG data indicative of the balance of the user satisfies the at least one threshold COG offset value, provide a signal to the first plurality of electrodes and the second plurality of electrodes to apply the first electrical pulse stimulation protocol and the second electrical pulse stimulation protocol.

4. The wearable device of claim 3, wherein the controller is further configured to generate at least a portion of the baseline COG profile by: identifying, based at least in part on the COG data generated by the one or more sensors one or more centers-of-gravity for the user; and establishing the at least one threshold COG offset value.

5. The wearable device of claim 3, wherein the controller is further configured to:
monitor the COG data generated by the one or more sensors after applying the signal to the first plurality of electrodes and the second plurality of electrodes; and
update the baseline COG profile to define electrical pulse characteristics to be associated with the at least one threshold COG offset value.

6. The wearable device of claim 1, wherein the controller is configured to identify the user wearing the wearable device based at least in part on data received from a user computing entity in wireless communication with the wearable device.

7. The wearable device of claim 1, wherein the first plurality of electrodes and the second plurality of electrodes each encompass neuromuscular electrical stimulation electrodes.

8. The wearable device of claim 1, wherein the controller is further configured to wirelessly communicate with a mobile device.

9. The wearable device of claim 1, wherein the controller is configured to select at least one electrical pulse stimulation protocol from a plurality of electrical pulse stimulation protocols based at least in part on a determination of a threshold COG offset value satisfied by the COG data.

10. A method comprising:
providing a wearable device around a waist of the user, the wearable device comprising:
a webbing extending between a first end and a second end, wherein the first end and the second end comprise fastening components that interact to enable connection between the first end and the second end to secure the webbing around a waist of a user such that the webbing defines an interior surface to be placed against a body of the user and an opposite exterior surface when the first end is connected with the second end;
a controller secured to the webbing;
one or more sensors in electronic communication with the controller, wherein the one or more sensors are secured to the webbing and configured to generate center of gravity (COG) data indicative of a balance of the user;
a first plurality of electrodes secured on the interior surface of the webbing, wherein (a) the first plurality of electrodes is in electronic communication with the controller, (b) the first plurality of electrodes is configured to cause delivery of electrical pulses in accordance with a first electrical pulse stimulation protocol responsive to a first signal from the controller, (c) the first signal is provided from the controller responsive to a determination that a fall event for the user is likely, and (d) the electrical pulses in accordance with the first electrical pulse stimulation protocol are configured to stimulate a first target muscle group of the user; and
a second plurality of electrodes secured on the interior surface of the webbing, wherein (a) the second plurality of electrodes is in electronic communication with the controller, (b) the second plurality of electrodes is configured to cause delivery of electrical pulses in accordance with a second electrical pulse stimulation protocol responsive to a determination that the fall event for the user is likely, and (d) the electrical pulses in accordance with the second electrical pulse stimulation protocol are configured to stimulate a second target muscle group of the user;
monitoring COG data generated by the one or more sensors via the controller;
determining, via the controller, whether the COG data satisfies at least one threshold COG offset value of a plurality of COG offset values;
responsive to determining that the COG data satisfies at least one threshold COG offset value, identifying the first electrical pulse stimulation protocol for the first plurality of electrodes of the wearable device and the second electrical pulse stimulation protocol for the second plurality of electrodes of the wearable device, wherein: (a) the first electrical pulse stimulation protocol is defined within a baseline COG profile and is configured to stimulate a first set of target muscles of the user's body, (b) the second electrical pulse stimulation protocol is defined within the baseline COG profile and is configured to stimulate a second set of target muscles of the user's body, and (c) the controller is configured to modify the first electrical pulse stimulation protocol and the second electrical pulse stimulation protocol based at least in part on a muscle condition of the user; and responsive to identifying the first electrical pulse stimulation protocol and the second electrical pulse stimulation protocol, causing (a) the first plurality of electrodes to provide a first electrical pulse corresponding to the first modified electrical pulse stimulation protocol, and (b) the second plurality of electrodes to provide a second electrical pulse corresponding to the second modified electrical pulse stimulation protocol.

11. The method of claim 10, wherein the wearable device further comprises a third plurality of electrodes (i) secured on the interior surface of the webbing, (ii) in electronic communication with the controller' and (iii) configured to apply a third electrical pulse stimulation protocol configured to stimulate a third target muscle group of the user upon receipt of signals from the controller.

12. The method of claim 10, wherein the controller is in electronic communication with a management computing entity storing baseline COG profiles for each of a plurality of users, and wherein the method further comprises:

receive a baseline COG profile for the user wearing the wearable device, wherein the baseline COG profile defines at least one threshold COG offset value;

compare, in real-time, the COG data indicative of the balance of the user with the at least one threshold COG offset value of the baseline COG profile for the user; and upon determining that the COG data indicative of the balance of the user satisfies the at least one threshold COG offset value, provide a signal to the first plurality of electrodes and the second plurality of electrodes to apply the first electrical pulse stimulation protocol and the second electrical pulse stimulation protocol.

13. The method of claim 12, further comprising generating at least a portion of the baseline COG profile by: identifying, based at least in part on the COG data generated by the one or more sensors one or more centers-of-gravity for the user; and establishing the at least one threshold COG offset value.

14. The method of claim 12, further comprising:

monitoring the COG data generated by the one or more sensors after applying the signal to the first plurality of electrodes and the second plurality of electrodes; and updating the baseline COG profile to define electrical pulse characteristics to be associated with the at least one threshold COG offset value.

15. The method of claim 10, further comprising identifying the user wearing the wearable device based at least in part on data received from a user computing entity in wireless communication with the wearable device.

16. The method of claim 10, further comprising selecting at least one electrical pulse stimulation protocol from a plurality of electrical pulse stimulation protocols based at least in part on a determination of a threshold COG offset value satisfied by the COG data.

17. The wearable device of claim 1, wherein the first signal from the controller and the second signal from the controller are a same signal.

* * * * *

UNITED STATES PATENT AND TRADEMARK OFFICE
CERTIFICATE OF CORRECTION

| | |
|---|---|
| PATENT NO. | : 11,896,815 B2 |
| APPLICATION NO. | : 17/248863 |
| DATED | : February 13, 2024 |
| INVENTOR(S) | : Aditya Madhuranthakam et al. |

It is certified that error appears in the above-identified patent and that said Letters Patent is hereby corrected as shown below:

On the Title Page

Under Item (57) change 17 claims to 16 claims.

In the Claims

At Column 33, Line 23, Claim 2, delete "controller'" and insert -- controller, --, therefor.

At Column 33, Lines 32-34, Claim 3, delete "receive a baseline COG profile for the user wearing the wearable device, wherein the baseline COG profile defines" and insert -- receive, for the user wearing the wearable device, a baseline COG profile defining --, therefor.

At Column 33, Line 37, Claim 3, delete "of the baseline COG profile for the user".

At Column 33, Lines 39-40, Claim 3, delete "upon determining that the COG data indicative of the balance of the user" and insert -- responsive to determining that the COG data --, therefor.

At Column 33, Line 48, Claim 4, delete "sensors one" and insert -- sensors, one --, therefor.

At Column 34, Lines 9-10, Claim 10, delete "A method comprising: providing a wearable device around a waist of the user," and insert -- A method comprising: determining, via a controller of a wearable device coupled with a waist of the user, whether center of gravity (COG) data obtained using the wearable device satisfies at least one threshold COG offset value of a plurality of COG offset values, --, therefor.

At Column 34, Line 16, Claim 10, delete "a waist of a user" and insert -- the waist of the user --, therefor.

At Column 34, Line 21, Claim 10, delete "a controller" and insert -- the controller --, therefor.

Signed and Sealed this
Ninth Day of July, 2024

*Katherine Kelly Vidal*
Katherine Kelly Vidal
*Director of the United States Patent and Trademark Office*

CERTIFICATE OF CORRECTION (continued)
U.S. Pat. No. 11,896,815 B2

At Column 34, Lines 24-25, Claim 10, delete "center of gravity (COG) data" and insert -- COG data --, therefor.

At Column 34, Lines 28-29, Claim 10, delete "is in electronic communication with the controller, (b) the first plurality of electrodes is configured" and insert -- is (i) in electronic communication with the controller, and (ii) configured --, therefor.

At Column 34, Line 32, Claim 10, delete "(c)" and insert -- (b) --, therefor.

At Column 34, Lines 35-36, Claim 10, delete "(d) the electrical pulses in accordance with the first electrical pulse stimulation protocol" and insert -- (c) the electrical pulses --, therefor.

At Column 34, Lines 40-42, Claim 10, delete "is in electronic communication with the controller, (b) the second plurality of electrodes is configured" and insert -- is (i) in electronic communication with the controller, and (ii) configured --, therefor.

At Column 34, Line 44, Claim 10, delete "responsive to a determination" and insert -- responsive to a second signal from the controller, (b) the second signal provided from the controller responsive to the determination --, therefor.

At Column 34, Line 45, Claim 10, delete "(d)" and insert -- (c) --, therefor.

At Column 34, Lines 52-53, Claim 10, delete "satisfies at least one threshold COG offset value of a plurality of COG offset values" and insert -- satisfies the at least one threshold COG offset value of the plurality of COG offset values --, therefor.

At Column 34, Lines 54-55, Claim 10, delete "satisfies at least one" and insert -- satisfies the at least one --, therefor.

At Column 34, Line 63, Claim 10, delete "the user's body" and insert -- the body of the user --, therefor.

At Column 34, Line 66, Claim 10, delete "the user's body" and insert -- the body of the user --, therefor.

At Column 35, Line 15, Claim 11, delete "controller'" and insert -- controller, --, therefor.

At Column 35, Lines 23-25, Claim 12, delete "receive a baseline COG profile for the user wearing the wearable device, wherein the baseline COG profile defines" and insert -- receiving, for the user wearing the wearable device, the baseline COG profile defining the --, therefor.

At Column 35, Line 26, Claim 12, delete "compare" and insert -- comparing --, therefor.

At Column 35, Line 28, Claim 12, delete "of the baseline COG profile for the user".

At Column 35, Lines 30-31, Claim 12, delete "upon determining that the COG data indicative of the

CERTIFICATE OF CORRECTION (continued)
U.S. Pat. No. 11,896,815 B2 balance of the user satisfies" and insert -- responsive to determining that the COG data satisfies --, therefor.

At Column 36, Line 1, Claim 12, delete "provide" and insert -- providing --, therefor.

At Column 36, Line 8, Claim 13, delete "sensors one" and insert -- sensors, one --, therefor.

At Column 36, Lines 27-29, delete Claim 17, "17. The wearable device of claim 1, wherein the first signal from the controller and the second signal from the controller are a same signal.".